US006300483B1

(12) United States Patent
Ludwig et al.

(10) Patent No.: US 6,300,483 B1
(45) Date of Patent: Oct. 9, 2001

(54) COMPOSITIONS INDUCING CLEAVAGE OF RNA MOTIFS

(75) Inventors: János Ludwig, Göttingen; Brian S. Sproat, Adelebsen, both of (DE)

(73) Assignee: Ribozyme Pharmaceuticals, Inc., Boulder, CO (US)

( * ) Notice: Subject to any disclaimer, the term of this patent is extended or adjusted under 35 U.S.C. 154(b) by 0 days.

(21) Appl. No.: 08/879,078

(22) Filed: Jun. 19, 1997

(51) Int. Cl.$^7$ .................................................... C07H 21/02
(52) U.S. Cl. ........................................ 536/23.1; 536/23.1
(58) Field of Search ................... 435/6; 514/44; 536/23.1, 23.2, 24.5, 25.1

(56) References Cited

U.S. PATENT DOCUMENTS

| 5,089,386 | * | 2/1992 | Stackebrandt et al. ................. 435/6 |
| 5,246,921 | * | 9/1993 | Reddy et al. ........................... 514/44 |
| 5,334,711 | * | 8/1994 | Sproat et al. ....................... 536/24.5 |
| 5,472,840 |   | 12/1995 | Stefano .................................... 435/6 |
| 5,545,729 | * | 8/1996 | Goodchild et al. ................. 536/24.4 |
| 5,591,623 |   | 1/1997 | Bennett ............................. 435/240.2 |

FOREIGN PATENT DOCUMENTS

WO 97/18312     5/1997 (WO).

OTHER PUBLICATIONS

Yang et al. "Minimum ribonucleotide requirement for catalysis by the RNA hammerhead domain" Biochemistry vol. 31, pp. 5005–5009, 1992.*

Ruffner et al. "Sequence requirement of the hammerhead RNA self–cleavage reaction", Biochemistry, vol. 29, pp. 106985–10702, 1990.*

Branch, "A good antisense molecule is hard to find," TIBS 23:45–50 (1998).

Flory, et al., "Nuclease–resistant ribozymes decrease stromelysin mRNA levels in rabbit synovium following exogenous delivery to the knee joint" *Proc. Natl. Acad. Sci. USA* 93: 754–758 (1996).

May, et al., "Anti–β–interferon antibodies inhibit the increased expression of HLA–B7 mRNA in tumor necrosis factor–treated human fibroblasts: Structural studies of the $\beta_2$ interferon involved," *Proc. Natl. Acad. Sci., USA* 83:8957–8961 (1986).

(List continued on next page.)

Primary Examiner—Jezia Riley
(74) Attorney, Agent, or Firm—McDonnell Boehnen Hulbert & Berghoff

(57) ABSTRACT

Disclosed are compositions inducing cleavage of an RNA substrate, as well as their use for inducing cleavage of RNA substrates in vitro and in vivo. The compositions contain part of an active center, with the other part of the active center provided by the RNA substrate. The subunits of the active center region of the compositions are nucleotides and/or nucleotide analogues. The disclosed compositions also have flanking regions contributing to the formation of a specific hybridization with an RNA substrate. Preferred compositions form, in combination with an RNA substrate, a structure resembling a hammerhead structure. The active center of the disclosed compositions is characterized by the presence of $I^{15.1}$ which allows cleavage of RNA substrates having $C^{16.1}$.

16 Claims, 3 Drawing Sheets

OTHER PUBLICATIONS

Offensperger, et al., "In vivo inhibition of duck hepatitis B virus replication and gene expression by phosphorate modified antisense oligodeoxynucleotides" *EMBO J.* 12(3):1257–1262 (1993).

Sànchez–Blàzquez, et al., "In Vivo Injection of Antisense Oligodeoxynucleotides to Ga Subunits and Supraspinal Analgesia Evoked by Mu and Delta Opioid Agonists" *J. Pharmacol. Exp. Ther.* 275(3):1590–1596 (1995).

Schwab, et al., "Characterization of an Inteleukin–6–Mediated Autocrine Growth Loop in the Human Multiple Myeloma Cell Line, U266," *Blood* 77(3):587–593 (1991).

Schwab, et al, "Antisense oligonucleotides adsorbed to polyalkylcyanoacrylate nanoparticles specifically inhibit mutated Ha–ras–mediated cell proliferation and tumorigenicity in nude mice" *Proc. Natl. Acad. Sci. USA* 91:10460–10464 (1994).

Standifer, et al., "Selective Loss of δOpioid Analgesia and Binding by Antisense Oligodeoxynucleotides to a δOpioid Receptor," *Neuron* 12:805–810 (1994).

Staunton, et al, "Primary Structure of ICAM–1 Demontrates Interaction between Members of the Immunoglobulin and integrin Supergene Families," *Cell* 52:925–933 (1988).

Stepkowski, et al., "Blocking of Heart Allograft Rejection by intercellular Adhesion Molecule–1 Antisense Oligonucleotides Alone or in Combination with Other Immunosuppressive Modalities" *J. Immunology* 153:5336–5346 (1994).

Uhlenback, "A small catalytic oligoribonucleotide," *Nature* 328(13):596–600 (1987).

Zhang, et al., "Antisense oligodeoxynucleotide reduces brain dopamaine $D_2$ receptors: behavioral correlates" *Neuroscience Letters* 161:223–226 (1993).

Zhou, et al., "In vivo Administration of an Oligodeoxynucleotide Antisense to the $D_2$ Dopamine Receptor Messenger RNA Inhibits $D_2$ Dopamine Receptor–Mediated Behavior and the Expression of $D_2$ Dopamine Receptors in Mouse Striatum" *J. Pharmacol. Exp. Ther.* 268(2):1015–1023 (1994).

Ludwig, et al., "Extending the cleavage rules for the hammerhead ribozyme: mutating adenosine$^{15.1}$ to inosine$^{15.1}$ changes the cleavage site specificity from $N^{16.2}U^{16.1}H^{17}$ to $N^{16.2}C^{16.1}H^{17}$," *Nucleic Acids Research* 26(10): 2279–2285 (1998).

\* cited by examiner

SEQUENCE LISTING

<160> NUMBER OF SEQ ID NOS: 21

<210> SEQ ID NO 1
<211> LENGTH: 57
<212> TYPE: RNA
<213> ORGANISM: Artificial Sequence
<220> FEATURE:
<223> OTHER INFORMATION: Description of Artificial Sequence: Hammerhead
      ribozyme
<221> NAME/KEY: unsure
<222> LOCATION: (1)..(57)
<223> OTHER INFORMATION: all n's stand for a, u, g, or c.

<400> SEQUENCE: 1
nnnnnnnnnn nnnnncuga nganrnnnnn nnnnnnnyng aarnnnnnnn nnnnnuh          57

<210> SEQ ID NO 2
<211> LENGTH: 14
<212> TYPE: RNA
<213> ORGANISM: Artificial Sequence
<220> FEATURE:
<223> OTHER INFORMATION: Description of Artificial Sequence: oligomer

```
         that induces cleavage of the RNA substrate
<221> NAME/KEY: unsure
<222> LOCATION: (1)..(14)
<223> OTHER INFORMATION: all n's, other than the n at position 10, stand
      for for a, u, g, or c.
<221> NAME/KEY: modified_base
<222> LOCATION: (10)
<223> OTHER INFORMATION: n stands for i

<400> SEQUENCE: 2
nnnnyngaan nnnn                                                         14

<210> SEQ ID NO 3
<211> LENGTH: 35
<212> TYPE: RNA
<213> ORGANISM: Artificial Sequence
<220> FEATURE:
<223> OTHER INFORMATION: Description of Artificial Sequence: RNA
      substrate
<221> NAME/KEY: unsure
<222> LOCATION: (1)..(35)
<223> OTHER INFORMATION: all n's stand for a, u, g, or c.

<400> SEQUENCE: 3
nnnnchnnnn nnnnnnnnnn nncugangan rnnnn                                  35

<210> SEQ ID NO 4
<211> LENGTH: 14
<212> TYPE: RNA
<213> ORGANISM: Artificial Sequence
<220> FEATURE:
<223> OTHER INFORMATION: Description of Artificial Sequence:
      oligonucleotide substrate
<221> NAME/KEY: misc_feature
<222> LOCATION: (14)
<223> OTHER INFORMATION: n stands for 3'-3' inverted thymidine

<400> SEQUENCE: 4
gaauaccggu cgcn                                                         14

<210> SEQ ID NO 5
<211> LENGTH: 14
<212> TYPE: RNA
<213> ORGANISM: Artificial Sequence
<220> FEATURE:
<223> OTHER INFORMATION: Description of Artificial Sequence:
      oligonucleotide substrate
<221> NAME/KEY: misc_feature
<222> LOCATION: (14)
<223> OTHER INFORMATION: n stands for 3'-3' inverted thymidine

<400> SEQUENCE: 5
gaauacaggu cgcn                                                         14

<210> SEQ ID NO 6
<211> LENGTH: 14
<212> TYPE: RNA
<213> ORGANISM: Artificial Sequence
<220> FEATURE:
<223> OTHER INFORMATION: Description of Artificial Sequence:
      oligonucleotide substrate
<221> NAME/KEY: misc_feature
<222> LOCATION: (14)
<223> OTHER INFORMATION: n stands for 3'-3' inverted thymidine

<400> SEQUENCE: 6
gaauacuggu cgcn                                                         14

<210> SEQ ID NO 7
```

```
<211> LENGTH: 14
<212> TYPE: RNA
<213> ORGANISM: Artificial Sequence
<220> FEATURE:
<223> OTHER INFORMATION: Description of Artificial Sequence:
      oligonucleotide substrate
<221> NAME/KEY: misc_feature
<222> LOCATION: (14)
<223> OTHER INFORMATION: n stands for 3'-3' inverted thymidine

<400> SEQUENCE: 7
gaaugccggu cgcn                                                     14

<210> SEQ ID NO 8
<211> LENGTH: 14
<212> TYPE: RNA
<213> ORGANISM: Artificial Sequence
<220> FEATURE:
<223> OTHER INFORMATION: Description of Artificial Sequence:
      oligonucleotide substrate
<221> NAME/KEY: misc_feature
<222> LOCATION: (14)
<223> OTHER INFORMATION: n stands for 3'-3' inverted thymidine

<400> SEQUENCE: 8
gaaugcaggu cgcn                                                     14

<210> SEQ ID NO 9
<211> LENGTH: 14
<212> TYPE: RNA
<213> ORGANISM: Artificial Sequence
<220> FEATURE:
<223> OTHER INFORMATION: Description of Artificial Sequence:
      oligonucleotide substrate
<221> NAME/KEY: misc_feature
<222> LOCATION: (14)
<223> OTHER INFORMATION: n stands for 3'-3' inverted thymidine

<400> SEQUENCE: 9
gaaugcuggu cgcn                                                     14

<210> SEQ ID NO 10
<211> LENGTH: 14
<212> TYPE: RNA
<213> ORGANISM: Artificial Sequence
<220> FEATURE:
<223> OTHER INFORMATION: Description of Artificial Sequence:
      oligonucleotide substrate
<221> NAME/KEY: misc_feature
<222> LOCATION: (14)
<223> OTHER INFORMATION: n stands for 3'-3' inverted thymidine

<400> SEQUENCE: 10 gaucccggu cgcn                                                      14

<210> SEQ ID NO 11
<211> LENGTH: 14
<212> TYPE: RNA
<213> ORGANISM: Artificial Sequence
<220> FEATURE:
<223> OTHER INFORMATION: Description of Artificial Sequence:
      oligonucleotide substrate
<221> NAME/KEY: misc_feature
<222> LOCATION: (14)
<223> OTHER INFORMATION: n stands for 3'-3' inverted thymidine

<400> SEQUENCE: 11
gaauccaggu cgcn                                                     14
```

```
<210> SEQ ID NO 12
<211> LENGTH: 14
<212> TYPE: RNA
<213> ORGANISM: Artificial Sequence
<220> FEATURE:
<223> OTHER INFORMATION: Description of Artificial Sequence:
      oligonucleotide substrate
<221> NAME/KEY: misc_feature
<222> LOCATION: (14)
<223> OTHER INFORMATION: n stands for 3'-3' inverted thymidine

<400> SEQUENCE: 12
gaauccuggu cgcn                                                        14

<210> SEQ ID NO 13
<211> LENGTH: 14
<212> TYPE: RNA
<213> ORGANISM: Artificial Sequence
<220> FEATURE:
<223> OTHER INFORMATION: Description of Artificial Sequence:
      oligonucleotide substrate
<221> NAME/KEY: misc_feature
<222> LOCATION: (14)
<223> OTHER INFORMATION: n stands for 3'-3' inverted thymidine

<400> SEQUENCE: 13
gaauuccggu cgcn                                                        14

<210> SEQ ID NO 14
<211> LENGTH: 14
<212> TYPE: RNA
<213> ORGANISM: Artificial Sequence
<220> FEATURE:
<223> OTHER INFORMATION: Description of Artificial Sequence:
      oligonucleotide substrate
<221> NAME/KEY: misc_feature
<222> LOCATION: (14)
<223> OTHER INFORMATION: n stands for 3'-3' inverted thymidine

<400> SEQUENCE: 14
gaauucaggu cgcn                                                        14

<210> SEQ ID NO 15
<211> LENGTH: 14
<212> TYPE: RNA
<213> ORGANISM: Artificial Sequence
<220> FEATURE:
<223> OTHER INFORMATION: Description of Artificial Sequence:
      oligonucleotide substrate
<221> NAME/KEY: misc_feature
<222> LOCATION: (14)
<223> OTHER INFORMATION: n stands for 3'-3' inverted thymidine

<400> SEQUENCE: 15
gaauucuggu cgcn                                                        14

<210> SEQ ID NO 16
<211> LENGTH: 14
<212> TYPE: RNA
<213> ORGANISM: Artificial Sequence
<220> FEATURE:
<223> OTHER INFORMATION: Description of Artificial Sequence:
      oligonucleotide substrate
<221> NAME/KEY: misc_feature
<222> LOCATION: (14)
<223> OTHER INFORMATION: n stands for 3'-3' inverted thymidine

<400> SEQUENCE: 16
gaaugucggu cgcn                                                        14
```

```
<210> SEQ ID NO 17
<211> LENGTH: 35
<212> TYPE: RNA
<213> ORGANISM: Artificial Sequence
<220> FEATURE:
<223> OTHER INFORMATION: Description of Artificial Sequence:
      Catalytic Oligomer
<221> NAME/KEY: modified_base
<222> LOCATION: (29)
<223> OTHER INFORMATION: n stands for i
<221> NAME/KEY: misc_feature
<222> LOCATION: (35)
<223> OTHER INFORMATION: n stands for 3'-3' inverted thymidine

<400> SEQUENCE: 17
gcgacccuga ugaggccgug aggccgaanu auucn                             35

<210> SEQ ID NO 18
<211> LENGTH: 35
<212> TYPE: RNA
<213> ORGANISM: Artificial Sequence
<220> FEATURE:
<223> OTHER INFORMATION: Description of Artificial Sequence:
      Catalytic Oligomer
<221> NAME/KEY: modified_base
<222> LOCATION: (29)
<223> OTHER INFORMATION: n stands for i
<221> NAME/KEY: misc_feature
<222> LOCATION: (35)
<223> OTHER INFORMATION: n stands for 3'-3' inverted thymidine

<400> SEQUENCE: 18
gcgacccuga ugaggccgug aggccgaanc auucn                             35

<210> SEQ ID NO 19
<211> LENGTH: 35
<212> TYPE: RNA
<213> ORGANISM: Artificial Sequence
<220> FEATURE:
<223> OTHER INFORMATION: Description of Artificial Sequence:
      Catalytic Oligomer
<221> NAME/KEY: modified_base
<222> LOCATION: (29)
<223> OTHER INFORMATION: n stands for i
<221> NAME/KEY: misc_feature
<222> LOCATION: (35)
<223> OTHER INFORMATION: n stands for 3'-3' inverted thymidine

<400> SEQUENCE: 19
gcgacccuga ugaggccgug aggccgaang auucn                             35

<210> SEQ ID NO 20
<211> LENGTH: 35
<212> TYPE: RNA
<213> ORGANISM: Artificial Sequence
<220> FEATURE:
<223> OTHER INFORMATION: Description of Artificial Sequence:
      Catalytic Oligomer
<221> NAME/KEY: modified_base
<222> LOCATION: (29)
<223> OTHER INFORMATION: n stands for i
<221> NAME/KEY: misc_feature
<222> LOCATION: (35)
<223> OTHER INFORMATION: n stands for 3'-3' inverted thymidine

<400> SEQUENCE: 20
gcgacccuga ugaggccgug aggccgaana auucn                             35

<210> SEQ ID NO 21
<211> LENGTH: 35
```

```
-continued

<212> TYPE: RNA
<213> ORGANISM: Artificial Sequence
<220> FEATURE:
<223> OTHER INFORMATION: Description of Artificial Sequence:
      Catalytic Oligomer
<221> NAME/KEY: misc_feature
<222> LOCATION: (35)
<223> OTHER INFORMATION: n stands for 3'-3' inverted thymidine

<400> SEQUENCE: 21
gcgacccuga ugaggccgug aggccgaaac auucn                              35
```

COMPOSITIONS INDUCING CLEAVAGE OF RNA MOTIFS

BACKGROUND OF THE INVENTION

The present invention is in the field of compositions having RNA-cleavage activity.

Hammerhead ribozymes are an example of catalytic RNA molecules which are able to recognize and cleave a given specific RNA substrate (Hotchins et al., *Nucleic Acids Res.* 14:3627 (1986); Keese and Symons, in *Viroids and viroid—like pathogens* (J. J. Semanchik, publ., CRC-Press, Boca Raton, Fla., 1987), pages 1–47). The catalytic center of hammerhead ribozymes is flanked by three stems and can be formed by adjacent sequence regions of the RNA or also by regions which are separated from one another by many nucleotides. FIG. 1 shows a diagram of such a catalytically active hammerhead structure. The stems have been denoted I, II and III. The nucleotides are numbered according to the standard nomenclature for hammerhead ribozymes (Hertel et al., *Nucleic Acids Res.* 20:3252 (1992)). In this nomenclature, bases are denoted by a number which relates their position relative to the 5' side of the cleavage site. Furthermore, each base that is involved in a stem or loop region has an additional designation (which is denoted by a decimal point and then another number) that defines the position of that base within the stem or loop. A designation of $N^{11.3}$ would indicate that this base is involved in a paired region and that it is the third base in that stem going away for the core region. This accepted convention for describing hammerhead derived ribozymes allows for the nucleotides involved in the core of the enzyme to always have the same number relative to all of the other nucleotides. The size of the stems involved in substrate binding or core formation can be any size and of any sequence, and the position of $A^9$, for example, will remain the same relative to all of the other core nucleotides. Nucleotides designated, for example, $N^{\wedge 12}$ or $N^{9\wedge}$ represent an inserted nucleotide where the position of the carrot (^) relative to the number denotes whether the insertion is before or after the indicated nucleotide. Thus, $N^{\wedge 12}$ represents a nucleotide inserted before nucleotide position 12, and $N^{9\wedge}$ represent a nucleotide inserted after nucleotide position 9.

The consensus sequence of the catalytic core structure is described by Ruffner and Uhlenbeck (*Nucleic Acids Res.* 18:6025–6029 (1990)). Perrirnan et al. (*Gene* 113:157–163 (1992)) have meanwhile shown that this structure can also contain variations, for example, naturally occurring nucleotide insertions such as $N^{9\wedge}$ and $N^{\wedge 12}$. Thus, the positive strand of the satellite RNA of the tobacco ring-spot virus does not contain any of the two nucleotide insertions while the +RNA strand of the virusoid of the lucerne transient streak virus (vLTSV) contains a $N^{9\wedge}$=U insertion which can be mutated to C or G without loss of activity (Sheldon and Symons, *Nucleic Acids Res.* 17:5679–5685 (1989)). Furthermore, in this special case, $N^7$=A and $R^{15.1}$=A. On the other hand, the minus strand of the carnation stunt associated viroid (-CarSV) is quite unusual since it contains both nucleotide insertions, that is $N^{\wedge 12}$=A and $N^{9\wedge}$=C (Hernandez et al., *Nucleic Acids Res.* 20:6323–6329 (1992)). In this viroid $N^7$=A and $R^{15.1}$=A. In addition, this special hammerhead structure exhibits a very effective self-catalytic cleavage despite the more open central stem.

Possible uses of hammerhead ribozymes include, for example, generation of RNA restriction enzymes and the specific inactivation of the expression of genes in, for example, animal, human or plant cells and prokaryotes, yeasts and plasmodia. A particular biomedical interest is based on the fact that many diseases, including many forms of tumors, are related to the overexpression of specific genes. Inactivating such genes by cleaving the associated mRNA represents a possible way to control and eventually treat such diseases. Moreover there is a great need to develop antiviral, antibacterial and antifungal pharmaceutical agents. Ribozymes have potential as such anti-infective agents since viral expression can be blocked selectively by cleaving viral or microbial RNA molecules vital to the survival of the organism can be selectively destroyed.

In addition to needing the correct hybridizing sequences for substrate binding, substrates for hammerhead ribozymes have been shown to strongly prefer the triplet $N^{16.2}U^{16.1}H^{17}$ where N can be any nucleotide, U is uridine, and H is either adenosine, cytidine, or uridine (Koizumi et al., *FEBS Lett.* 228, 228–230 (1988); Ruffner et al., *Biochemistry* 29, 10695–10702 (1990); Perriman et al., *Gene* 113, 157–163 (1992)). The fact that changes to this general rule for substrate specificity result in non-functional substrates implies that there are "non core compatible" structures which are formed when substrates are provided which deviate from the stated requirements. Evidence along these lines was recently reported by Uhlenbeck and co-workers (*Biochemistry* 36:1108–1114 (1997)) when they demonstrated that the substitution of a G at position 17 caused a functionally catastrophic base pair between $G^{17}$ and $C^3$ to form, both preventing the correct orientation of the scissile bond for cleavage and the needed tertiary interactions of $C^3$ (Murray et al., *Biochem. J.* 311:487–494 (1995)). The strong preference for a U at position 16.1 may exist for similar reasons. Many experiments have been done in an attempt to isolate ribozymes which are able to efficiently relieve the requirement of a U at position 16.1, however, attempts to find hammerhead type ribozymes which can cleave substrates having a base other than a U at position 16.1 have proven impossible (Perriman et al., *Gene* 113, 157–163 (1992)).

Efficient catalytic molecules with reduced or altered requirements in the cleavage region are highly desirable because their isolation would greatly increase the number of available target sequences that molecules of this type could cleave. For example, it would be desirable to have a ribozyme variant that could efficiently cleave substrates containing triplets other than $N^{16.2}U^{16.1}H^{17}$ since this would increase the number of potential target cleavage sites.

Chemically modified oligonucleotides which contain a block of deoxyribonucleotides in the middle region of the molecule have potential as pharmaceutical agents for the specific inactivation of the expression of genes (Giles et al., *Nucleic Acids Res.* 20:763–770 (1992)). These oligonucleotides can form a hybrid DNA-RNA duplex in which the DNA bound RNA strand is degraded by RNase H. Such oligonucleotides are considered to promote cleavage of the RNA and so cannot be characterized as having an RNA-cleaving activity nor as cleaving an RNA molecule (the RNase H is cleaving). A significant disadvantage of these oligonucleotides for in vivo applications is their low specificity, since hybrid formation, and thus cleavage, can also take place at undesired positions on the RNA molecules.

Previous attempts to recombinantly express catalytically active RNA molecules in the cell by transfecting the cell with an appropriate gene have not proven to be very effective since a very high expression was necessary to inactivate specific RNA substrates. In addition the vector systems which are available now cannot generally be applied. Furthermore, unmodified ribozymes cannot be administered directly due to the sensitivity of RNA to degradation by RNases and their interactions with proteins. Thus, chemically modified active substances have to be used in order to administer hammerhead ribozymes exogenously (discussed, for example, by Heidenreich et al., *J. Biol. Chem.* 269:2131–2138 (1994); Kiehntopf et al., *EMBO J.* 13:4645–4652 (1994); Paolella et al., *EMBO J.* 11:1913–1919 (1992); and Usman et al., *Nucleic Acids Symp. Ser.* 31:163–164 (1994)).

U.S. Pat. No. 5,334,711 describes such chemically modified active substances based on synthetic catalytic oligonucleotide structures with a length of 35 to 40 nucleotides which are suitable for cleaving a nucleic acid target sequence and contain modified nucleotides that contain an optionally substituted alkyl, alkenyl or alkynyl group with 1–10 carbon atoms at the 2'-O atom of the ribose. These oligonucleotides contain modified nucleotide building blocks and form a structure resembling a hammerhead structure. These oligonucleotides are able to cleave specific RNA substrates. Examples of oligonucleotides are described having an active center which has a length of 14 nucleotides and which contains several ribonucleotides. These ribonucleotides increase the sensitivity of the oligonucleotide to enzymes which cleave RNA. A further disadvantage is the length of the active center which can often lead to unspecific hybridization.

WO 95/11304 describes RNA-cleaving nucleic acids with an active center that is free of ribonucleotide building blocks but instead contains deoxyribonucleotides. However, the deoxyribonucleotides used in the active center result in a very low RNA cleavage activity. Thus, it was reported that a 13-mer deoxyribozyme of the "GAAA" type based on LTSV was not able to cleave a 41-mer oligoribonucleotide substrate while the corresponding 13-mer ribozyme exhibited catalytic activity (Jeffries and Symons, *Nucleic Acids Res.* 17:1371–1377 (1989)).

WO 97/18312 describes oligomers which contain only part of a catalytic core resembling a hammerhead catalytic core. These oligomers, when associated with an RNA substrate having a motif resembling the complementary part of a catalytic core, induce cleavage of the RNA substrate. The RNA substrates for use with these oligomers all have a U at position 16.1.

The use of a large number of deoxyribonucleotides in the hybridization arms or in the active center can lead to a loss of specificity due to an activation of RNase H since sequences which are related to the desired target sequence can also be cleaved. Moreover, catalytic DNA oligomers are not particularly well suited for in vivo applications due to interactions with proteins, and lack of resistance to degradation by nucleases.

The shortest ribozymes that have been previously used have a minimum length of 15+N+M nucleotides, the active center being 15 nucleotides long and N and M being the length of the recognition sequences (Benseler et al., *J. Am. Chem. Soc.* 115:8483–8484 (1993)). Such ribozymes also contain ribonucleotides in at least five positions of the catalytic center (Paolella et al., *EMBO J.* 11:1913–1919 (1992), and Yang et al., *Bio-chemistry* 31:5005–5009 (1992)).

It is therefore an object of the present invention to provide compositions that induce cleavage of RNA, and in particular to provide oligomers that induce cleavage of RNA and which at the same time have a high stability, activity, and specificity.

It is another object of the present invention to provide compositions that induce cleavage of RNA substrates having a cleavage site triplet other than $N^{16.2}U^{16.1}H^{17}$.

SUMMARY OF THE INVENTION

Disclosed are compositions inducing cleavage of an RNA substrate, as well as their use for inducing cleavage of RNA substrates in vitro and in vivo. The compositions contain part of an active center, with the other part of the active center provided by the RNA substrate. The subunits of the active center region of the compositions are nucleotides and/or nucleotide analogues. The disclosed compositions also have flanking regions contributing to the formation of a specific hybridization with an RNA substrate. Preferred compositions form, in combination with an RNA substrate, a structure resembling a hammerhead structure. The active center of the disclosed compositions is characterized by the presence of $I^{15.1}$ which allows cleavage of RNA substrates having $C^{16.1}$.

DETAILED DESCRIPTION OF THE INVENTION

Figure 1:
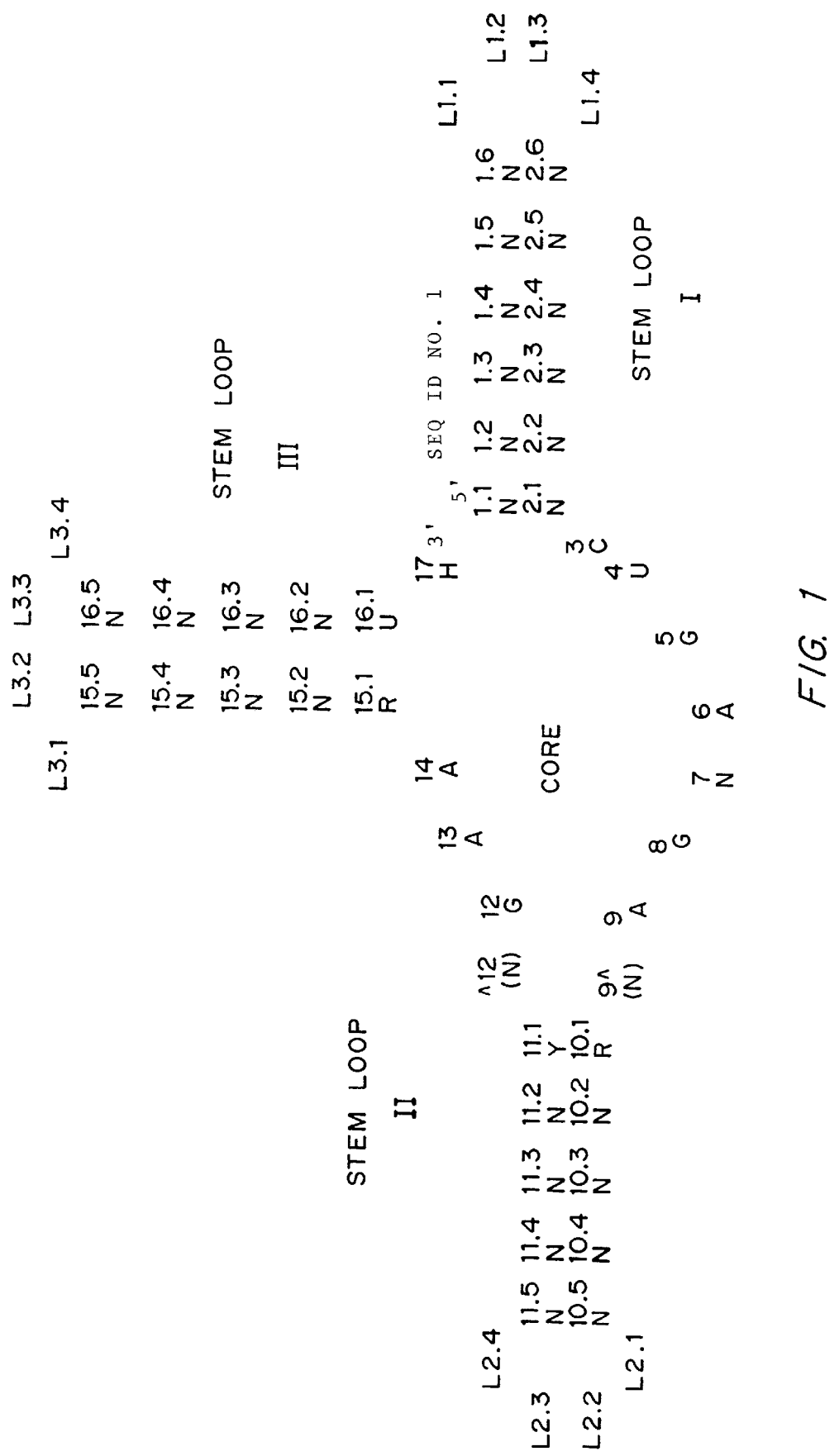
FIG. 1 is a diagram of a hammerhead structure and the corresponding nomenclature (SEQ ID NO:1). Cleavage occurs between $H^{17}$ and $N^{1.1}$ to generate the 2'-3'-cyclic phosphate at H17.

Disclosed are compositions inducing cleavage of an RNA substrate, as well as their use for inducing cleavage of RNA substrates in vitro and in vivo. The compositions contain part of an active center, with the other part of the active center provided by the RNA substrate. The subunits of the active center region of the compositions are nucleotides and/or nucleotide analogues. The disclosed compositions also have flanking regions contributing to the formation of a specific hybridization with an RNA substrate. Preferred compositions form, in combination with an RNA substrate, a structure resembling a hammerhead structure. The active center of the disclosed compositions is characterized by the presence of $I^{15.1}$ which allows cleavage of RNA substrates having $C^{16.1}$.

All naturally occurring hammerhead ribozymes have an $A^{15.1}$-$U^{16.1}$ base pair. In addition, it is known that substrates for ribozymes based on the consensus hammerhead sequence strongly prefer a substrate that contains an $N^{16.2}U^{16.1}H^{17}$ triplet in which $H^{17}$ is not a guanosine (Koizumi et aL, *FEBS Lett.* 228, 228–230 (1988); Ruffner et al., *Biochemistry* 29, 10695–10702 (1990); Perriman et al., *Gene* 113, 157–163 (1992)). Many experiments have been done in an attempt to isolate ribozymes which are able to efficiently relieve the requirement of a U at position 16.1, however, attempts to find ribozymes which can cleave substrates having a base other than a U at position 16.1 have proven impossible (Perriman et al., *Gene* 113, 157–163 1992, Singh et al., *Antisense and Nucleic Acid Drug Development* 6:165–168 (1996)).

However, examination of the recently published X-ray crystal structures (Pley et al., *Nature* 372:68–74 (1994), Scott et al., *Cell* 81:991–1002 (1995), and Scott et al., *Science* 274:2065–2069 (1996)) led to the realization that the $A^{15.1}$-$U^{16.1}$ interaction is a non-standard base pair with a single hydrogen bond between the exocyclic amine (N6) of the adenosine and the 4-oxo group of the uridine. Modeling studies (based on the crystal structure) then led to the discovery that the interaction of the wild-type $A^{15.1}$-$U^{16.1}$ base pair can be spatially mimicked by replacement with an $I^{15.1}$-$C^{16.1}$ base pair that adopts an isostructural orientation and which preserves the required contact of the 2-keto group of $C^{16.1}$ with $A^6$ of the uridine turn. In the model, the polarity of the stabilizing hydrogen bond between positions 15.1 and 16.1 is reversed in the $I^{15.1}$-$C^{16.1}$ interaction, but the correct orientation of the bases around this bond is maintained.

It has been discovered that Gerlach type ribozyme analogues containing an inosine at position 15.1 readily cleave RNA substrates containing an $N^{16.2}C^{16.1}H^{17}$ triplet. Based on this, disclosed are compositions, preferably synthetic oligomers, which induce cleavage of a nucleic acid target sequence containing the structure 5'-$Z_3$'-$C^{16.1}$-$X^{17}$-S-$Z_4$-$Z_1$'-3' where S is capable of forming a stem and loop and $Z_4$ corresponds to part of an active center. It is preferred that $X^{17}$ is not guanosine. The ability to induce cleavage of substrates having $N^{16.2}C^{16.1}X^{17}$ triplets effectively doubles the number of targets available for cleavage using compositions of the type disclosed.

Compositions Inducing RNA Cleavage in a Substrate

Specifically disclosed is a composition that induces cleavage of an RNA substrate, where the composition includes a structure 5'-$Z_1$-$Z_2$-$Z_3$-3'. Elements $Z_1$ and $Z_3$ are each oligomeric sequences which are made up of nucleotides, nucleotide analogues, or a combination of both, or are oligonucleotide analogues. The oligomeric sequences of elements $Z_1$ and $Z_3$ specifically interact with the RNA substrate, preferably by hybridization.

In these preferred compositions, element $Z_2$ has a structure of

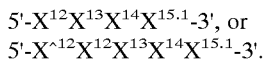, or

5'-$X^{\wedge 12}X^{12}X^{13}X^{14}X^{15.1}$-3'.

Element $Z_2$ in these preferred compositions is made up of nucleotides, nucleotide analogues, or a combination of both. The nucleotides and nucleotide analogues in element $Z_2$ each have the structure

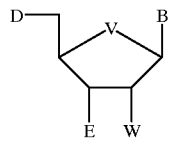 (I)

In structure (I) each B can be adenin-9-yl, cytosin-1-yl, guanin-9-yl, uracil-1-yl, uracil-5-yl, hypoxanthin-9-yl, thymin-1-yl, 5-methylcytosin-1-yl, 2,6-diaminopurin-9-yl, purin-9-yl, 7-deazaadenin-9-yl, 7-deazaguanin-9-yl, 5-propynylcytosin-1-yl, 5-propynyluracil-1-yl, isoguanin-9-yl, 2-aminopurin-9-yl, 6-methyluracil-1-yl, 4-thiouracil-1-yl, 2-pyrimidone-1-yl, quinazoline- 2,4-dione-1-yl, xanthin-9-yl, $N^2$-dimethylguanin-9-yl or a functional equivalent thereof;

Each V can be an O, S, NH, or $CH_2$ group.

Each W can be —H, —OH, —COOH, —$CONH_2$, —$CONHR^1$, —$CONR^1R^2$, —$NH_2$, —$NHR^1$, —$NR^1R^2$, —$NHCOR^1$, —SH, $SR^1$, —F, —$ONH_2$, —$ONHR^1$, —$ONR^1R^2$, —NHOH, —$NHOR^1$, —$NR^2OH$, —$NR^2OR^1$, substituted or unsubstituted $C_1$–$C_{10}$ straight chain or branched alkyl, substituted or unsubstituted $C_2$–$C_{10}$ straight chain or branched alkenyl, substituted or unsubstituted $C_2$–$C_{10}$ straight chain or branched alkynyl, substituted or unsubstituted $C_1$–$C_{10}$ straight chain or branched alkoxy, substituted or unsubstituted $C_2$–$C_{10}$ straight chain or branched alkenyloxy, and substituted or unsubstituted $C_2$–$C_{10}$ straight chain or branched alkynyloxy. The substituents for W groups are independently halogen, cyano, amino, carboxy, ester, ether, carboxamide, hydroxy, or mercapto. $R^1$ and $R^2$ can be substituted or unsubstituted alkyl, alkenyl, or alkynyl groups, where the substituents are independently halogen, cyano, amino, carboxy, ester, ether, carboxamide, hydroxy, or mercapto.

D and E are residues which together form a phosphodiester or phosphorothioate diester bond between adjacent nucleosides or nucleoside analogues or together form an analogue of an internucleosidic bond.

B is hypoxanthin-9-yl, or a functional equivalent thereof, in $X^{15.1}$; B can be guanin-9-yl, hypoxanthin-9-yl or 7-deazaguanin-9-yl in $X^{12}$; B can be adenin-9-yl, 2,6-diaminopurin-9-yl, purin-9-yl or 7-deazaadenin-9-yl in $X^{13}$ and $X^{14}$; and B can be adenin-9-yl, cytosin-1-yl, guanin-9-yl, uracil-1-yl, uracil-5-yl, hypoxanthin-9-yl, thymin-1-yl, 5-methylcytosin-1-yl, 2,6-diaminopurin-9-yl, purin-9-yl, 7-deazaadenin-9-yl, 7-deazaguanin-9-yl, 5-propynylcytosin-1-yl, 5-propynyluracil-1-yl, isoguanin-9-yl, 2-aminopurin-9-yl, 6-methyluracil-1-yl, 4-thiouracil-1-yl, 2-pyrimidone-1-yl, quinazoline-2,4-dione-1-yl, xanthin-9-yl, $N^2$-dimethylguanin-9-yl or a functional equivalent thereof in $X^{\wedge 12}$. B of $X^{15.1}$ is preferably an analog of hypoxanthin-9-yl, preferably where no hydrogen bond can form between any group at the 2 position of the base and the 2-oxo group of $C^{16.1}$. Preferably, B is not guanin-9-yl in $X^{15.1}$.

B in $X^{12}$, $X^{13}$, and $X^{14}$ can also be a functionally equivalent nucleobase within the context of the catalytic core of a hammerhead ribozyme.

The disclosed compositions have significant advantages. For example, the disclosed compositions require only 4+N+M or 5+N+M monomeric units (for example, nucleotides) in which N and M are preferably numbers in the range of 5 to 10. Furthermore, the disclosed compositions can contain a significantly smaller number of natural ribonucleotides without loss of activity. Due to the reduced length and reduced number of ribonucleotides, the disclosed compositions are more conveniently and easily synthesized, and can be more stable in vivo, than Gerlach type ribozymes. The in vivo stability can be increased by a further reduction in the number of ribonucleotides.

DEFINITIONS

As used herein, oligomer refers to oligomeric molecules composed of subunits where the subunits can be of the same class (such as nucleotides) or a mixture of classes. It is preferred that the disclosed oligomers be oligomeric sequences. It is more preferred that the disclosed oligomers be oligomeric sequences. Oligomeric sequences are oligomeric molecules where each of the subunits includes a nucleobase (that is, the base portion of a nucleotide or nucleotide analogue) which can interact with other oligomeric sequences in a base-specific manner. The hybridization of nucleic acid strands is a preferred example of such base-specific interactions. Oligomeric sequences preferably are comprised of nucleotides, nucleotide analogues, or both, or are oligonucleotide analogues.

As used herein, nucleoside refers to adenosine, guanosine, cytidine, uridine, 2'-deoxyadenosine, 2'-deoxyguanosine, 2'-deoxycytidine, or thymidine. A nucleoside analogue is a chemically modified form of nucleoside containing a chemical modification at any position on the base or sugar portion of the nucleoside. As used herein, the term nucleoside analogue encompasses, for example, both nucleoside analogues based on naturally occurring modified nucleosides, such as inosine and pseudouridine, and nucleoside analogues having other modifications, such as modifications at the 2' position of the sugar. As used herein, nucleotide refers to a phosphate derivative of nucleosides as described above, and a nucleotide analogue is a phosphate derivative of nucleoside analogues as described above. The subunits of oligonucleotide analogues, such as peptide nucleic acids, are also considered to be nucleotide analogues.

As used herein, a ribonucleotide is a nucleotide having a 2' hydroxyl function. Analogously, a 2'-deoxyribonucleotide is a nucleotide having only 2' hydrogens. Thus, ribonucleotides and deoxyribonucleotides as used herein refer to naturally occurring nucleotides having nucleoside components adenosine, guanosine, cytidine, and uridine, or 2'-deoxyadenosine, 2'-deoxyguanosine, 2'-deoxycytidine, and thymidine, respectively, without any chemical modification. Ribonucleosides, deoxyribonucleosides, ribonucleoside analogues and deoxyribonucleoside analogues are similarly defined except that they lack the phosphate group, or an analogue of the phosphate group, found in nucleotides and nucleotide analogues.

As used herein, oligonucleotide analogues are polymers of nucleic acid-like material with nucleic acid-like properties, such as sequence dependent hybridization, that contain at one or more positions, a modification away from a standard RNA or DNA nucleotide. A preferred example of an oligonucleotide analogue is peptide nucleic acid.

Figure 3:
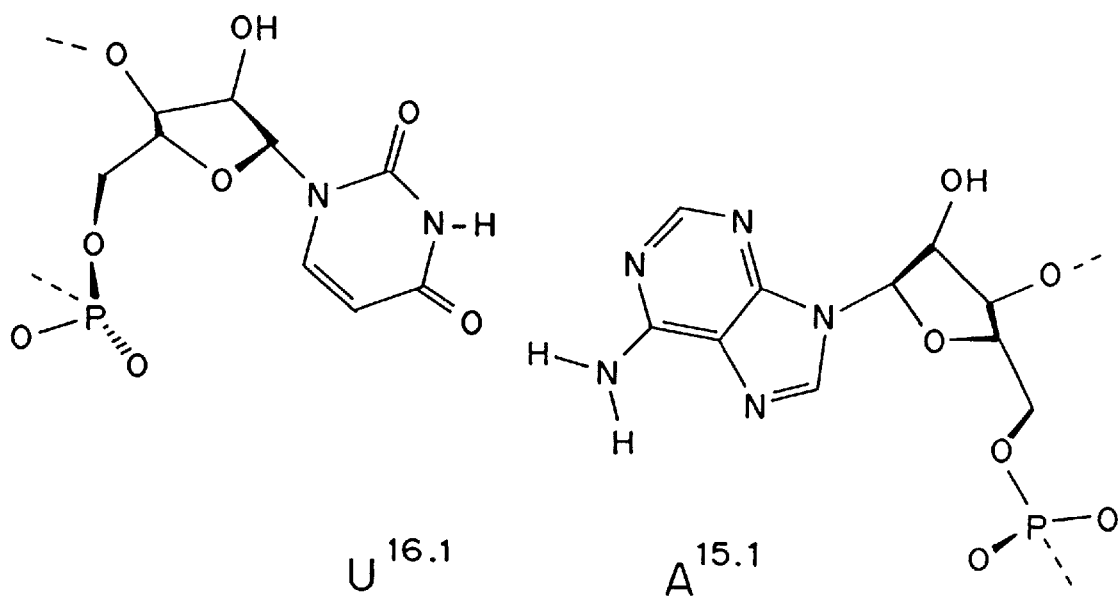
FIG. 3 is a diagram showing the interaction of the $A^{15.1}$-$U^{16.1}$ base pair in hammerhead ribozymes (top), and the predicted isostructural interaction of a $I^{15.1}$-$C^{16.1}$ base pair (bottom) that replaces the $A^{15.1}$-$U^{16.1}$ base pair.
Figure 3:
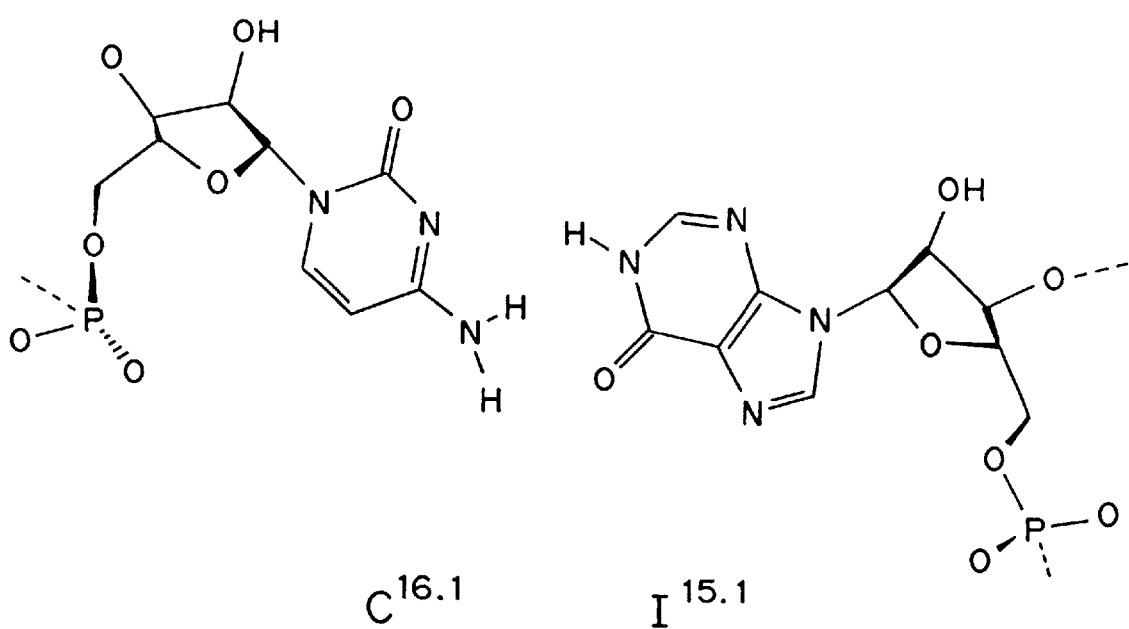

As used herein, base pair refers to a pair of nucleotides or nucleotide analogues which interact through one or more hydrogen bonds. The term base pair is not limited to interactions generally characterized as Watson-Crick base pairs, but includes non-canonical or sheared base pair interactions (Topal and Fresco, Nature 263:285 (1976); Lomant and Fresco, Prog. Nucl. Acid Res. Mol. Biol. 15:185 (1975)). Thus, nucleotides $A^{15.1}$ and $U^{16.1}$ form a base pair in hammerhead ribozymes (see FIG. 1) but the base pair is non-canonical (see FIG. 3).

The internucleosidic linkage between two nucleosides can be achieved by phosphodiester bonds or by modified phospho bonds such as by phosphorothioate groups or other bonds such as, for example, those described in U.S. Pat. No. 5,334,711.

Flanking Elements $Z_1$ and $Z_3$

The monomeric subunits of elements $Z_1$ and $Z_3$ which flank the active center (formed by element $Z_2$) are preferably nucleotides and/or nucleotide analogues. Elements $Z_1$ and $Z_3$ are designed so that they specifically interact, preferably by hybridization, with a given RNA substrate and, together with the element $Z_2$, form a structure (preferably a structure resembling part of a hammerhead ribozyme) which induces specific cleavage of the RNA substrate.

The subunits of elements $Z_1$ and $Z_3$ can, on the one hand, be ribonucleotides. However, it is preferred that the number of ribonucleotides be as small as possible since the presence of ribonucleotides reduces the in vivo stability of the oligomers. Elements $Z_1$ and $Z_3$ (and also the active center $Z_2$) preferably do not contain any ribonucleotides at the positions containing pyrimidine nucleobases. Such positions preferably contain nucleotide analogues.

The use of a large number of deoxyribonucleotides in elements $Z_1$ and $Z_3$ is also less preferred since undesired interactions with proteins can occur or an unintended RNase H-sensitive DNA-RNA hybrid could form. Thus, elements $Z_1$ and $Z_3$ each preferably contain (1) no ribonucleotides, and (2) no sequences of more than 3 consecutive deoxyribonucleotides.

The subunits of elements $Z_1$ and $Z_3$ are preferably nucleotides, nucleotide analogues, or a combination. Preferably, the nucleotides and nucleotide analogues in elements $Z_1$ and $Z_3$ each have the structure

(I)

In structure (I) each B can be adenin-9-yl, cytosin-1-yl, guanin-9-yl, uracil-1-yl, uracil-5-yl, hypoxanthin-9-yl, thymin-1-yl, 5-methylcytosin-1-yl, 2,6-diaminopurin-9-yl, purin-9-yl, 7-deazaadenin-9-yl, 7-deazaguanin-9-yl, 5-propynylcytosin-1-yl, 5-propynyluracil-1-yl, isoguanin-9-yl, 2-aminopurin-9-yl, 6-methyluracil-1-yl, 4-thiouracil-1-yl, 2-pyrimnidone-1-yl, quinazoline-2,4-dione-1-yl, xanthin-9-yl, $N^2$-dimethylguanin-9-yl or a functional equivalent thereof;

Each V can be an O, S, NH, or $CH_2$ group.

Each W can be —H, —OH, —COOH, —$CONH_2$, —$CONHR^1$, —$CONR^1R^2$, —$NH_2$, —$NHR^1$, —$NR^1R^2$, —$NHCOR^1$, —SH, $SR^1$, —F, —$ONH_2$, —$ONHR^1$, —$ONR^1R^2$, —NHOH, —$NHOR^1$, —$NR^2OH$, —$NR^2OR^1$, substituted or unsubstituted $C_1$–$C_{10}$ straight chain or branched alkyl, substituted or unsubstituted $C_2$–$C_{10}$ straight chain or branched alkenyl, substituted or unsubstituted $C_2$–$C_{10}$ straight chain or branched alkynyl, substituted or unsubstituted $C_1$–$C_{10}$ straight chain or branched alkoxy, substituted or unsubstituted $C_2$–$C_{10}$ straight chain or branched alkenyloxy, and substituted or unsubstituted $C_2$–$C_{10}$ straight chain or branched alkynyloxy. The substituents for W groups are independently halogen, cyano, amino, carboxy, ester, ether, carboxamide, hydroxy, or mercapto. $R^1$ and $R^2$ can be substituted or unsubstituted alkyl, alkenyl, or alkynyl groups, where the substituents are independently halogen, cyano, amino, carboxy, ester, ether, carboxamide, hydroxy, or mercapto.

D and E are residues which together form a phosphodiester or phosphorothioate diester bond between adjacent nucleosides or nucleoside analogues or together form an analogue of an internucleosidic bond.

For elements $Z_1$ and $Z_3$ having nucleotide and/or nucleotide analogues of structure (I), it is preferred that each W is substituted or unsubstituted $C_1$–$C_{10}$ straight chain or branched alkoxy, $C_2$–$C_{10}$ straight chain or branched alkenyloxy, or $C_2$–$C_{10}$ straight chain or branched alkynyloxy.

In addition, the flanking elements $Z_1$ and $Z_3$ can also contain nucleotide analogues such as peptide nucleic acids (also referred to as peptidic nucleic acids; see for example Nielsen et al., Science 254:1497–1500 (1991), and Duehohn et al., J. Org. Chem. 59:5767–5773 (1994)). In this case the coupling of individual subunits can, for example, be achieved by acid amide bonds. Elements $Z_1$ and $Z_3$, when based on peptide nucleic acids, can be coupled to element $Z_2$, based on nucleotides or nucleotide analogues, using either suitable linkers (see, for example, Petersen et al., BioMed. Chem. Lett. 5:1119–1121 (1995)) or direct coupling (Bergmann et al., Tetrahedron Lett. 36:6823–6826 (1995)). Where elements $Z_1$ and $Z_3$ contain a combination of nucleotides (and/or nucleotide analogues) and peptide nucleic acid, similar linkages can be used to couple the different parts.

The subunits of the flanking elements $Z_1$ and $Z_3$ contain nucleobases or nucleobase analogues which can hybridize or interact with nucleobases that occur naturally in RNA molecules. The nucleobases are preferably selected from naturally occurring bases (that is, adenine, guanine, cytosine, thymine and uracil) as well as nucleobase analogues, such as 2,6-diaminopurine, hypoxanthine, 5-methylcytosine, pseudouracil, 5-propynyluracil, and 5-propynylcytosine, which enable a specific binding to the target RNA.

A strong and sequence-specific interaction (that is, a more stable hybrid between the RNA substrate and the oligomer) between the RNA substrate and elements $Z_1$ and $Z_3$ is preferred. For this purpose, it is preferred that the following nucleobase analogues be used in oligomeric sequences of elements $Z_1$ and $Z_3$ in place of the standard nucleobases: 2,6-diaminopurine instead of adenine; thymine or 5-propynyluracil instead of uracil; and 5-methylcytosine or 5-propynylcytosine instead of cytosine. 2-Amino-2'-O-alkyladenosines are also preferred (Lamnim et al., Nucleic Acids Res. 19:3193–3198 (1991)). Furthermore, aromatic systems can be linked to positions 4 and 5 of uracil to produce nucleobase analogues such as phenoxazine, which can improve the stability of the double-strand (Lin et al., J. Am. Chem. Soc. 117:3873–3874 (1995)).

Preferred RNA substrates for cleavage using the disclosed compositions have the structure $5'-Z_3'-C^{16.1}-X^{17}-S-Z_4-Z_1'-3'$, where $Z_1'$ and $Z_3'$ interact with $Z_1$ and $Z_3$, respectively, where $C^{16.1}$ is cytidine, and where $X^{17}$ is adenosine, guanosine, cytidine, or uridine. S is an RNA sequence capable of forming a hairpin structure with a length of preferably from 6 to 60 and more preferably of from 6 to 20 bases. Cleavage occurs 3' of $X^{17}$. Preferably, $X^{17}$ is adenosine, cytidine, or uridine, more preferably $X^{17}$ is adenosine or cytidine, and most preferably $X^{17}$ is adenosine. Preferably, $X^{16.2}$ (that is, the 3' nucleoside in element $Z_3'$) is adenosine or guanosine. The target sites in substrates which can be cleaved using the disclosed compositions are distinct from target sites for hammerhead ribozymes since hammerhead ribozymes require a uridine in position 16.1 of the substrate.

Figure 2:
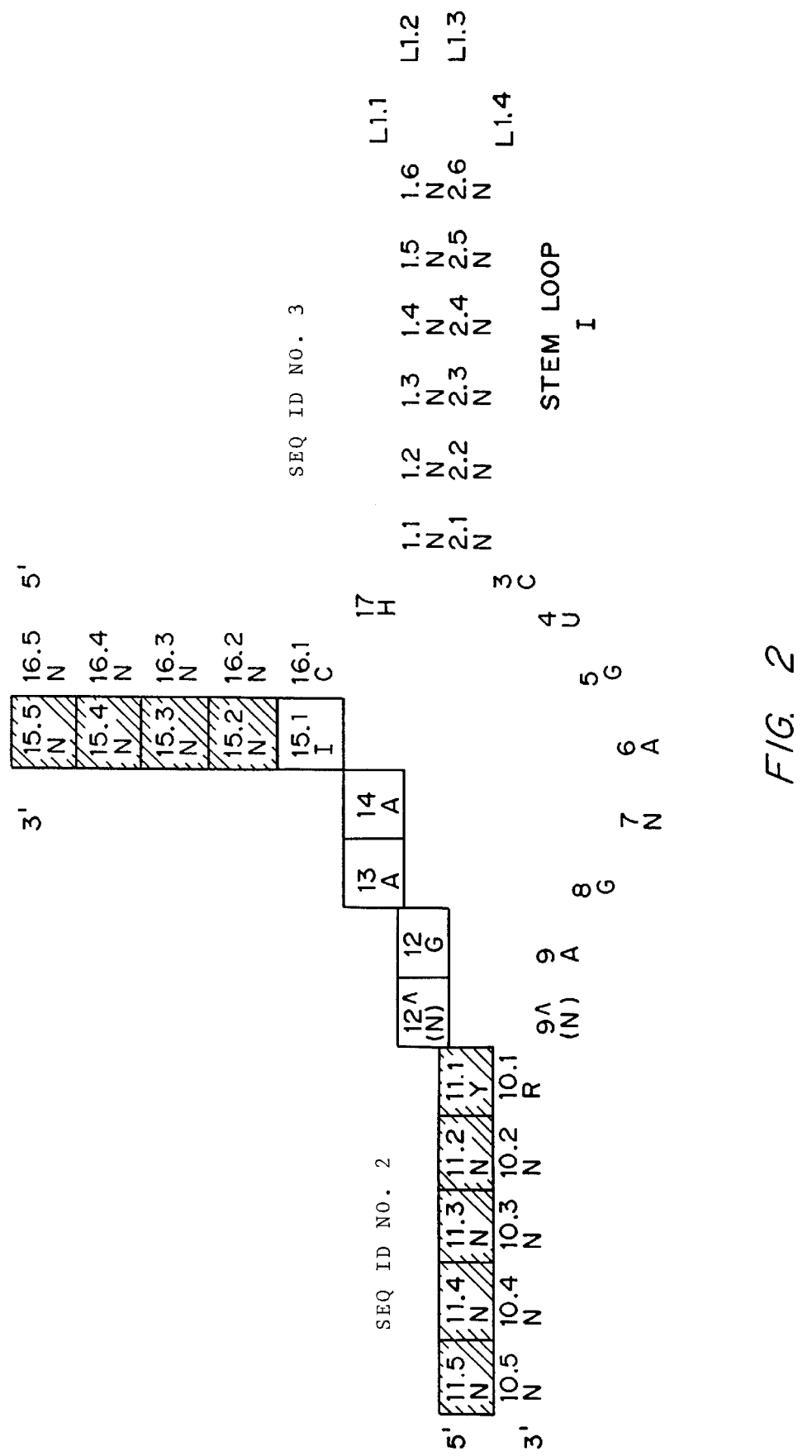
FIG. 2 is a diagram of an RNA substrate (SEQ ID NO:3) in association with an example of an oligomer (SEQ ID NO:2) that induces cleavage of the RNA substrate. The structure formed by the oligomer and the substrate resembles the structure of a hammerhead ribozyme, with each providing a part of the elements corresponding to the catalytic core. In this case, the substrate makes up half of stems II and III and all of stem I, and loops II and III are not present. Cleavage occurs 3' of $H^{17}$.

Element $Z_4$ of the substrate has the structure $5'-X^3X^4X^5X^6X^7X^8X^9-3'$, or
$5'-X^3X^4X^5X^6X^7X^8X^9X^{9\wedge}-3'$ where $X^5$ and $X^8$ are both guanosine, $X^6$ and $X^9$ are both adenosine, $X^4$ is uridine, $X^3$ is cytidine, and $X^7$ and $X^{9\wedge}$ are adenosine, guanosine, cytidine, or uridine. The disclosed composition, in combination with an RNA substrate containing a structure of element $Z_4$, can form a structure resembling a hammerhead as shown in FIG. 2.

It is preferred that $Z_1$ interact with $Z_1'$ in such a way as to stabilize the interactions between $Z_2$ and $Z_4$. Although preferred, it is not required that element $Z_1$ be present in the disclosed compositions. In this case, it is preferred that element $Z_1'$ (in the substrate) include a G at the 5' end (that is, at the junction of elements $Z_4$ and $Z_1'$). Taira and co-workers (Amontov and Taira, J. Am. Chem. Soc. 118:1624–1628 (1996)) have shown that the stacking energy gained from a guanosine juxtaposed to $R^9$ of a hammerhead-like ribozyme stabilizes the formation of a catalytic structure. Thus, it is preferred that the 5' nucleotide of $Z_1'$ is G.

The cleavage motif $C^{16.1}-X^{17}-S-Z_4$ occurs only rarely (approximately one motif for every 5000 to 10,000 nucleotides). This, taken together with the individually selected recognition sequences, means that, statistically, a composition as disclosed should induce cleavage of only the selected target RNA within the entire human RNA pool. Only an unproductive binding but no cleavage occurs at other potential binding sites, since $C^{16.1}$, $X^{17}$, and elements S and $Z_4$ are required for cleavage. In addition, the disclosed compositions need not activate RNase H since they can be made with a low content of deoxyribonucleotides. This prevents induction of any unwanted non-specific cleavage.

Computer algorithms can be used to identify RNA substrates in sequence databases suitable for use with the disclosed compositions. An example of such an algorithm is (using the numbering according to FIG. 2):

i: find all $C^3$ UGANGA(N)R sequences in a given mRNA;
ii: identify $N^{2.1}$ and find potential $N^{1.1}-N^{2.1}$ base pairs (in which $N^{1.1}$ must be part of an $N^{16.2}-C^{16.1}-H^{17}-N^{1.1}$ sequence) in a region positioned approximately 30 nucleotides from $C^3$ in the 3' direction;
iii: calculate stem stabilities for stems which terminate at the above-mentioned $N^{1.1}-N^{2.1}$ base pairs;
iv: sort according to stem stability.

A program based on these algorithms enables a very efficient search in databases or individual sequences. As a result, in addition to a suitable RNA target sequence, one obtains the sequence of the oligomer which is necessary to induce cleavage of this target sequence. In this connection it is important to also take into consideration potential target sites containing incomplete base pairs in the region of the stem structure (that is, element S) since several incomplete base pairs (mismatches) can be tolerated in this section.

Preferred RNA substrates for cleavage using the disclosed compositions are human cellular transcripts and transcripts of human or animal viruses as well as transcripts of bacteria and fungi that infect humans. Preferred RNA substrates are human dopamine D2 receptor MRNA, human brain cholecystokinin receptor MRNA, human serotonin 5-HT3 receptor mRNA, human alpha-2-macroglobulin receptor RNA, human tyrosine kinase-type receptor (HER2) mRNA, human interleukin 2 receptor beta chain mRNA, human MAD-3 mRNA, human bcl-1 mRNA, human bcl-2 mRNA, human cyclin F mRNA, human cyclin G1 mRNA, human bleomycin hydrolase mRNA, human acute myeloid leukemia 1 oncogene mRNA, human polycystic kidney disease 1 protein (PKD1) mRNA, transcripts of the bovine viral diarrhea virus, transcripts of the foot and mouth disease virus 3D gene and transcripts of the Epstein-Barr virus.

Particularly preferred cleavage motifs are located at the following positions of the RNA substrates (the name of the respective sequence in the EMBL Nucleotide Sequence Database 49th or 50th Edition is given in parentheses):

human dopamine D2 receptor mRNA (HSDRD2A) with $N^{16.2}$ at position 2355 and a cleavage after the triplet UCU;

human brain cholecystokinin receptor mRNA (HSBRACHE) with $N^{16.2}$ at position 1519 and a cleavage after the triplet ACA;

human serotonin 5-HT3 receptor mRNA (HSS5HT3RA) with $N^{16.2}$ at position 467 and a cleavage after the triplet ACA;

human alpha-2-macroglobulin receptor RNA (HS2MRUR08) with $N^{16.2}$ at position 776 and a cleavage after the triplet GCC;

human tyrosine kinase-type receptor (HER2) mRNA (HSHER2A) with $N^{16.2}$ at position 3330 and a cleavage after the triplet ACU;

human interleukin 2 receptor beta chain MnRNA (HSIL2RBC) with $N^{16.2}$ at position 937 and a cleavage after the triplet ACA;

human MAD-3 mRNA (HSMAD3A) with $N^{16.2}$ at position 138 and a cleavage after the triplet GCC;

human bcl-1 mRNA (HSBCL1G) with $N^{16.2}$ at position 777 and a cleavage after the triplet GCA;

human bcl-2 mRNA (HSBCL2A) with $N^{16.2}$ at position 4152 and a cleavage after the triplet ACC;

human cyclin F mRNA (HSCYCLF) with $N^{16.2}$ at position 378 and a cleavage after the triplet ACA;

human cyclin G1 mRNA (HSCYCGIR) with $N^{16.2}$ at position 166 and a cleavage after the triplet GCC;

human bleomycin hydrolase mRNA (HSBLEO) with $N^{16.2}$ at position 1352 and a cleavage after the triplet ACA;

human acute myeloid leukemia 1 oncogene mRNA (HSAML1) with $N^{16.2}$ at position 883 and a cleavage after the triplet GCC;

human polycystic kidney disease 1 protein mRNA (HSPKD1A) with $N^{16.2}$ at position 11354 and a cleavage after the triplet GCC;

transcripts of the bovine viral diarrhea virus (BV25053) with $N^{16.2}$ at position 616 and cleavage after the triplet GCC;

transcripts of the foot and mouth disease virus 3D gene (FMDV3D) with $N^{16.2}$ at position 1291 and a cleavage after the triplet GCA; and transcripts of the Epstein-Barr virus (HEEBVT2R) with $N^{16.2}$ at position 1647 and a cleavage after the triplet GCA.

Flanking elements $Z_1$ and $Z_3$ preferably contain, independently of each other, from 3 to 40, and more preferably from 5 to 10, nucleotides or nucleotide analogues. It is preferred that $Z_1$ and $Z_1'$ interact to form a stem of at least three base pairs, and that $Z_3$ and $Z_3'$ interact to form a stem of at least three base pairs. It is more preferred that these stems are adjacent to $Z_2$. It is most preferable that $Z_1$ and $Z_1'$ interact to form a stem of more than three base pairs, and that $Z_3$ and $Z_3'$ interact to form a stem of more than three base pairs.

Catalytic Core

Elements $Z_2$ and $Z_4$ are considered to form the catalytic core of the combination of a disclosed composition and an RNA substrate (see FIG. 2). $Z_2$ is preferably made up of nucleotide analogues. In element $Z_2$ it is preferred that each W (in structure (I)) is $C_1$–$C_5$ straight chain or branched alkyl, $C_2$–$C_5$ straight chain or branched alkenyl, $C_2$–$C_5$ straight chain or branched alkynyl, $C_1$–$C_5$ straight chain or branched alkoxy, $C_2$–$C_5$ straight chain or branched alkenyloxy, and $C_2$–$C_5$ straight chain or branched $C_2$–$C_5$ alkynyloxy. It is also preferred that in $X^{\hat{}12}$, W is $NH_2$, OH-substituted $C_1$–$C_4$ alkyl, OH-substituted $C_2$–$C_4$ alkenyl, OH-substituted $C_1$–$C_4$ alkoxy or OH-substituted $C_2$–$C_4$ alkenyloxy. It is more preferred that in $X^{\hat{}2}$, W is $NH_2$, methoxy, 2-hydroxyethoxy, allyloxy or allyl. It is also preferred that in $X^{12}$, W is —H or —OH. It is also preferred that in each $X^{13}$ and $X^{14}$, W is $C_1$–$C_4$ alkyl, $C_2$–$C_4$ alkenyl, $C_1$–$C_4$ alkoxy, $C_2$–$C_4$ alkenyloxy, OH-substituted $C_1$–$C_4$ alkyl, OH-substituted $C_2$–$C_4$ alkenyl, OH-substituted $C_1$–$C_4$ alkoxy, or OH-substituted $C_2$–$C_4$ alkenyloxy. It is more preferred that in each $X^{13}$ and $X^{14}$, W is methoxy, 2-hydroxyethoxy or allyloxy.

The subunits in element $Z_2$ are preferably nucleotide analogues which can only hybridize weakly with ribonucleotides. Examples of such subunits are nucleotide analogues that contain a substituted or unsubstituted alkyl, alkenyl, alkynyl, alkoxy, alkenyloxy or alkynyloxy group, with preferably 1 to 5 carbon atoms, at the 2' position of ribose. Preferred nucleobases which can be used in element $Z_2$ for this purpose are adenin-9-yl, purin-9-yl, guanin-9-yl and hypoxanthin-9-yl.

The following nucleotides and nucleotide analogues are preferred for element $Z_2$ (referring to components of structure (I)):

Position $X^{12}$: B=guanin-9-yl, V=O, W=H; B=7-deazaguanin-9-yl, V=O, W=OH; or B=guanin-9-yl, V=O, W=OH;

Position $X^{13}$: B=adenin-9-yl, V=O, W=allyloxy; or B=adenin-9-yl, V=O, W=2-hydroxyethoxy; B=purin-9-yl, V=O, W=allyloxy;

Position $X^{14}$: B=adenin-9-yl, V=O , W=allyloxy; B=purin-9-yl, V=O, W=OH; or B=adenin-9-yl, V=O, W=2-hydroxyethoxy; B=purin-9-yl, V=O, W=allyloxy;

Position $X^{15.1}$: B=hypoxanthin-9-yl or a functional equivalent thereof, V=O, W=OH.

Elements $Z_2$ and $Z_4$ interact in a way that allows for the formation of a catalytic structure. In preferred compositions $Z_2$ and $Z_4$ interact in a way that allows for the formation of a catalytic structure resembling a hammerhead catalytic structure. One way $Z_2$ and $Z_4$ can interact to form a catalytic structure is through the interaction of the nucleotides and/or nucleotide analogues making up $Z_2$ and the nucleotides making up $Z_4$. The disclosed compositions are able to induce cleavage of an RNA substrate independent of RNase H. That is, the disclosed compositions are able to induce cleavage of an RNA substrate without involving RNase H. Although the disclosed compositions may also be capable of promoting cleavage of RNA by RNase H, it is preferred that they do not.

The 3' end of the disclosed compositions can be protected against degradation by exonucleases by, for example, using a nucleotide analogue that is modified at the 3' position of the ribose sugar (for example, by including a substituted or unsubstituted alkyl, alkoxy, alkenyl, alkenyloxy, alkynyl or alkynyloxy group as defined above). The disclosed compositions can also be stabilized against degradation at the 3' end by exonucleases by including a 3'-3'-Iinked dinucleotide structure (Ortigao et al., *Antisense Research and Development* 2:129–146 (1992)) and/or two modified phospho bonds, such as two phosphorothioate bonds.

The disclosed compositions can also be linked to a prosthetic group in order to improve their cellular uptake and/or to enable a specific cellular localization. Examples of such prosthetic groups are polyamino acids (for example, polylysine), lipids, hormones or peptides. These prosthetic groups are usually linked via the 3' or 5' end of the oligomer either directly or by means of suitable linkers (for example, linkers based on 6-aminohexanol or 6-mercaptohexanol). These linkers are commercially available and techniques suitable for linking prosthetic groups to the oligomer are known to a person skilled in the art.

Increasing the rate of hybridization can be important for the biological activity of the disclosed compositions since in this way it is possible to achieve a higher activity at low concentrations of the composition. This is important for short-lived RNA substrates or RNA substrates that occur less often. A substantial acceleration of the hybridization can be achieved by, for example, coupling positively charged peptides (containing, for example, several lysine residues) to the end of an oligonucleotide (Corey *J. Am. Chem. Soc.* 117:9373–9374 (1995)). The disclosed compositions can be simply modified in this manner using the linkers described above. Alternatively, the rate of hybridization can also be increased by incorporation of subunits which contain sperminyl residues (Schmid and Behr, *Tetrahedron Lett.* 36:1447–1450 (1995)). Such modifications of the disclosed compositions also improve the ability to bind to RNA substrates having secondary structures.

Synthesis of Oligomers

The disclosed compositions can be synthesized using any suitable method. Many synthesis methods are known. The following techniques are preferred for synthesis of the disclosed compositions. 2'-O-Allyl modified oligomers that contain residual purine ribonucleotides, and bearing a suitable 3'-terminus such as an inverted thymidine residue (Ortigao et al., Antisense Research and Development 2:129–146 (1992)) or two phosphorothioate linkages at the 3'-terminus to prevent eventual degradation by 3'-exonucleases, can be synthesized by solid phase β-cyanoethyl phosphoramidite chemistry (Sinha et al., Nucleic Acids Res. 12:4539–4557 (1984)) on any commercially available DNA/RNA synthesizer. A preferred method is the 2'-O-tert-butyldimethylsilyl (TBDMS) protection strategy for the ribonucleotides (Usman et al., J. Am. Chem. Soc. 109:7845–7854 (1987)), and all the required 3'-O-phosphoramidites are commercially available. In addition, the use of aminomethylpolystyrene is preferred as the support material due to its advantageous properties (McCollum and Andrus Tetrahedron Letters 32:4069–4072 (1991)). Fluorescein can be added to the 5'-end of a substrate RNA during the synthesis by using commercially available fluorescein phosphoramidites. In general, a desired oligomer can be synthesized using a standard RNA cycle. Upon completion of the assembly, all base labile protecting groups are removed by an 8 hour treatment at 55° C. with concentrated aqueous ammonia/ethanol (3:1 v/v) in a sealed vial. The ethanol suppresses premature removal of the 2'-O-TBDMS groups which would otherwise lead to appreciable strand cleavage at the resulting ribonucleotide positions under the basic conditions of the deprotection (Usman et al., J. Am. Chem. Soc. 109:7845–7854 (1987)). After lyophilization the TBDMS protected oligomer is treated with a mixture of triethylamine trihydrofluoride/triethylamine/N-methylpyrrolidinone for 2 hours at 60° C. to afford fast and efficient removal of the silyl protecting groups under neutral conditions (Wincott et al., Nucleic Acids Res. 23:2677–2684 (1995)). The fully deprotected oligomer can then be precipitated with butanol according to the procedure of Cathala and Brunel (Nucleic Acids Res. 18:201 (1990)). Purification can be performed either by denaturing polyacrylamide gel electrophoresis or by a combination of ion-exchange HPLC (Sproat et al., Nucleosides and Nucleotides 14:255–273 (1995)) and reversed phase HPLC. For use in cells, it is preferred that synthesized oligomers be converted to their sodium salts by precipitation with sodium perchlorate in acetone. Traces of residual salts are then preferably removed using small disposable gel filtration columns that are commercially available. As a final step it is preferred that the authenticity of the isolated oligomers is checked by matrix assisted laser desorption mass spectrometry (Pieles et al., Nucleic Acids Res. 21:3191–3196 (1993)) and by nucleoside base composition analysis. In addition, a functional cleavage test with the oligomer and the corresponding chemically synthesized short oligoribonucleotide substrate is also preferred.

Cleavage of RNA Substrates

The disclosed compositions can have a very high in vivo activity since the RNA cleavage will be promoted by protein factors that are present in the nucleus or cytoplasm of the cell. Examples of such protein factors (which can increase the activity of hammerhead ribozymes) are, for example, the nucleocapsid protein NCp7 of HIV1 (Müller et al., J. Mol. Biol. 242:422–429 (1994)) and the heterogeneous nuclear ribonucleoprotein A1 (Heidenreich et al., Nucleic Acids Res. 23:2223–2228 (1995)). Thus, cleavage of long RNA transcripts can be efficiently induced within the cell by the disclosed compositions.

The disclosed compositions can be used in pharmaceutical compositions that contain one or several oligomers as the active substance, and, optionally, pharmaceutically acceptable auxiliary substances, additives and carriers. Such pharmaceutical compositions are suitable for the production of an agent to specifically inactivate the expression of genes in eukaryotes, prokaryotes and viruses, especially of human genes such as tumor genes or viral genes or RNA molecules in a cell. Further areas of application are the inactivation of the expression of plant genes or insect genes. Thus, the disclosed compositions can be used as drugs for humans and animals as well as a pesticide for plants.

A variety of methods are available for delivering the disclosed compositions to cells. For example, in general, the disclosed compositions can be incorporated within or on microparticles. As used herein, microparticles include liposomes, virosomes, microspheres and microcapsules formed of synthetic and/or natural polymers. Methods for making microcapsules and microspheres are known to those skilled in the art and include solvent evaporation, solvent casting, spray drying and solvent extension. Examples of useful polymers which can be incorporated into various microparticles include polysaccharides, polyanhydrides, polyorthoesters, polyhydroxides and proteins and peptides.

Liposomes can be produced by standard methods such as those reported by Kim et al., Biochim. Biophys. Acta, 728:339–348 (1983); Liu et al., Biochim. Biophys. Acta, 1104:95–101 (1992); and Lee et al., Biochim. Biophys. Acta., 1103:185–197 (1992); Wang et al., Biochem., 28:9508–9514 (1989)). Such methods have been used to deliver nucleic acid molecules to the nucleus and cytoplasm of cells of the MOLT-3 leukemia cell line (Thierry and Dritschilo, Nucl. Acids Res., 20:5691–5698 (1992)). Alternatively, the disclosed compositions can be incorporated within microparticles, or bound to the outside of the microparticles, either ionically or covalently.

Cationic liposomes or microcapsules are microparticles that are particularly useful for delivering negatively charged compounds such as the disclosed compounds, which can bind ionically to the positively charged outer surface of these liposomes. Various cationic liposomes have previously been shown to be very effective at delivering nucleic acids or nucleic acid-protein complexes to cells both in vitro and in vivo, as reported by Felgner et al., Proc. Natl. Acad. Sci. USA, 84:7413–7417 (1987); Felgner, Advanced Drug Delivery Reviews, 5:163–187 (1990); Clarenc et al., Anti-Cancer Drug Design, 8:81–94 (1993). Cationic liposomes or microcapsules can be prepared using mixtures including one or more lipids containing a cationic side group in a sufficient quantity such that the liposomes or microcapsules formed from the mixture possess a net positive charge which will ionically bind negatively charged compounds. Examples of positively charged lipids that may be used to produce cationic liposomes include the aminolipid dioleoyl phosphatidyl ethanolamine (PE), which possesses a positively charged primary amino head group; phosphatidylcholine (PC), which possess positively charged head groups that are not primary amines; and N[1-(2,3-dioleyloxy)propyl]-N,N,N-triethylammonium ("DOTMA," see Felgner et al., Proc. Natl. Acad. Sci USA, 84:7413–7417 (1987); Felgner et al., Nature, 337:387–388 (1989); Felgner, Advanced Drug Delivery Reviews, 5:163–187 (1990)).

A preferred form of microparticle for delivery of the disclosed compositions are heme-bearing microparticles. In these microparticles, heme is intercalated into or covalently conjugated to the outer surface of the microparticles. Heme-bearing microparticles offer an advantage in that since they are preferentially bound and taken up by cells that express the heme receptor, such as hepatocytes, the amount of drug required for an effective dose is significantly reduced. Such targeted delivery may also reduce systemic side effects that can arise from using relatively high drug concentrations in non-targeted delivery methods. Preferred lipids for forming heme-bearing iicroparticles are 1,2-dioleoyloxy-3-(trinethylammonium) propane (DOTAP) and dioleoyl phosphatidyl ethanolamine (DOPE). The production and use of heme-bearing microparticles are described in PCT application WO 95/27480 by Innovir.

The disclosed compositions can also be encapsulated by or coated on cationic liposomes which can be injected intravenously into a mammal. This system has been used to introduce DNA into the cells of multiple tissues of adult mice, including endothelium and bone marrow, where hematopoietic cells reside (see, for example, Zhu et al., *Science*, 261:209–211 (1993)).

Liposomes containing the disclosed compositions can be administered systemically, for example, by intravenous or intraperitoneal administration, in an amount effective for delivery of the disclosed compositions to targeted cells. Other possible routes include trans-dermal or oral, when used in conjunction with appropriate microparticles. Generally, the total amount of the liposome-associated oligomer administered to an individual will be less than the amount of the unassociated oligomer that must be administered for the same desired or intended effect.

Compositions including various polymers such as the polylactic acid and polyglycolic acid copolymers, polyethylene, and polyorthoesters and the disclosed compositions can be delivered locally to the appropriate cells by using a catheter or syringe. Other means of delivering such compositions locally to cells include using infusion pumps (for example, from Alza Corporation, Palo Alto, Calif.) or incorporating the compositions into polymeric implants (see, for example, Johnson and Lloyd-Jones, eds., *Drug Delivery Systems* (Chichester, England: Ellis Horwood Ltd., 1987), which can effect a sustained release of the therapeutic compositions to the immediate area of the implant.

For therapeutic applications the active substance is preferably administered at a concentration of 0.01 to 10,000 µg/kg body weight, more preferably of 0.1 to 1000 µg/kg body weight. The administration can, for example, be carried out by injection, inhalation (for example as an aerosol), as a spray, orally (for example as tablets, capsules, coated tablets etc.), topically or rectally (for example as suppositories).

The disclosed compositions can be used in a method for the specific inactivation of the expression of genes in which an active concentration of the composition is taken up into a cell so that the composition induces specific cleavage of a predetermined RNA molecule which is present in the cell, the cleavage preferably occurring catalytically. Similar compositions, which are described in U.S. Pat. No. 5,334,711, have been used successfully in mice to inactivate a gene (Lyngstadaas et al., *EMBO J*. 14:5224–5229 (1995)). This process can be carried out in vitro on cell cultures as well as in vivo on living organisms (prokaryotes or eukaryotes such as humans, animals or plants).

The disclosed compositions can also be used as RNA restriction enzymes to induce cleavage of RNA molecules (in, for example, cell free in vitro reactions). The disclosed compositions can also be used in a reagent kit for the restriction cleavage of RNA molecules which contains, for example, an oligomer and suitable buffer substances. In this case the oligomer and the buffer substances can be present in the form of solutions, suspensions or solids such as powders or lyophilisates. The reagents can be present together, separated from one another or optionally also on a suitable carrier. The disclosed compositions can also be used as a diagnostic agent or to identify the function of unknown genes.

The present invention will be further understood by reference to the following non-limiting examples.

EXAMPLES

The following examples demonstrate that compositions having motifs forming structures resembling hammerheads but which include $I^{15.1}$ and $C^{16.1}$ can result in specific cleavage of an RNA molecule. Although the examples involve the use of oligomers having RNA cleaving activity and including motifs corresponding to both elements $Z_2$ and $Z_4$ (the oligomers in the examples are thus analogous to a Gerlach type ribozyme), the activities are indicative of the cleavage inducing activity of the disclosed compositions.

Example 1

Cleavage Reactions Which Indicate that an Inosine Substitution at Position 15.1 can Effectively Cleave $N^{16.2}C^{16.1}H^{17}$.

A set of 12 substrates was synthesized which covered each permutation of the $N^{16.2}C^{16.1}H^{17}$ motif where $H^{17}$ is not guanosine. The oligomers and the corresponding substrates used in the cleavage assays are shown in Table 1. Each of the substrates was labeled with fluorescein at the 5' end and an inverted thymidine cap was used on the 3'-end. A set of four catalytic oligomers was synthesized, providing an appropriately matched catalytic oligomer for each of the substrates. Each of these catalytic oligomers had an inosine at position 15.1. The catalytic oligomers were similar to those described in U.S. Pat. No. 5,334,711 except for the substitution of I for A at position 15.1. The catalytic oligomers includes, in a single molecule, the equivalent of elements $Z_4$, $Z_1{'}$, $Z_1$, $Z_2$, and $Z_3$ in the compositions and RNA substrates as described above. A control substrate and catalytic oligomer were also synthesized in which there was a U at position 16.1 of the substrate and an A at position 15.1 of the catalytic oligomer.

TABLE 1

| $N^{16.2}N^{16.1}H^{17}$ Triplet | Substrate sequence | |
|---|---|---|
| ACC | Fl-GAAUACCGGUCGC*T | (SEQ ID NO:4) |
| ACA | Fl-GAAUACAGGUCGC*T | (SEQ ID NO:5) |
| ACU | Fl-GAAUACUGGUCGC*T | (SEQ ID NO:6) |
| GCC | Fl-GAAUGCCGGUCGC*T | (SEQ ID NO:7) |
| GCA | Fl-GAAUGCAGGUCGC*T | (SEQ ID NO:8) |
| GCU | Fl-GAAUGCUGGUCGC*T | (SEQ ID NO:9) |
| CCC | Fl-GAAUCCCGGUCGC*T | (SEQ ID NO:10) |
| CCA | Fl-GAAUCCAGGUCGC*T | (SEQ ID NO:11) |
| CCU | Fl-GAAUCCUGGUCGC*T | (SEQ ID NO:12) |
| UCC | Fl-GAAUUCCGGUCGC*T | (SEQ ID NO:13) |
| UCA | Fl-GAAUUCAGGUCGC*T | (SEQ ID NO:14) |
| UCU | Fl-GAAUUCUGGUCGC*T | (SEQ ID NO:15) |

TABLE 1-continued

| | | |
|---|---|---|
| GUC | Fl-GAAUGUCGGUCGC*T | (SEQ ID NO:16) |

| Targeted triplet | Catalytic oligomer sequence | |
|---|---|---|
| ACH | gcgacccuGAuGaggccgugaggccGaaIuauuc*T | (SEQ ID NO:17) |
| GCH | gcgacccuGAuGaggccgugaggccGaaIcauuc*T | (SEQ ID NO:18) |
| CCH | gcgacccuGAuGaggccgugaggccGaaIgauuc*T | (SEQ ID NO:19) |
| UCH | gcgacccuGAuGaggccgugaggccGaaIaauuc*T | (SEQ ID NO:20) |
| GUC | gcgacccuGAuGaggccgugaggccGaaAcauuc*T | (SEQ ID NO:21) |

Fl = Fluorescein label
*T = 3'-3'inverted thymidine
A, C, G, I, U = ribonucleotides (I is inosine)
a, c, g, u = 2'-O-allyl-ribonucleotides The above substrates and catalytic oligomers were used in cleavage reactions to determine the ability of an inosine at position 15.1 to overcome the requirement of a U at position 16.1 for cleavage. All of the reactions were performed using the following protocol. The reactions were typically done in 100 μl and they contained distilled, autoclaved $H_2O$, 10 mM $MgCl_2$, 10 mM Tris-HCl pH 7.4, 5 μM ribozyme, and 0.25 μM substrate. The catalytic oligomer, substrate, and buffer were added together and heated to 95° C. for 5 minutes. After cooling to room temperature over 5 minutes the reactions were brought to 10 mM $MgCl_2$, mixed, and placed at 37° C. 10 μL aliquots were removed at specific time intervals (10, 30, 60, and 120 minutes) and added to 3 μl of loading buffer (95% formamide, 100 mM EDTA pH 8.0, 0.05% bromophenol blue) to quench the reaction. Samples were analyzed by 20% polyacrylamide gel electrophoresis. Gels were analyzed on a Molecular Dynamics Fluorescence Imager. The results of cleavage reactions of this type, using the substrates and catalytic oligomers shown in Table 1, are shown in Table 2.

TABLE 2

| $N^{16.2}$ $N^{16.1}$ $H^{17}$ Triplet | After mixing | 10 | 30 | 60 | 120 |
|---|---|---|---|---|---|
| $I^{15.1}$ $U^{15.2}$ Catalytic oligomer | | | | | |
| ACC | 4.4 | 28.2 | 58.1 | 91.5 | 91.5 |
| ACA | 7.7 | 71.8 | 84.7 | 93.1 | 94.8 |
| ACU | 1.8 | | | 58.7 | 70.5 |
| $I^{15.1}$ $C^{15.2}$ Catalytic oligomer | | | | | |
| GCC | 1.62 | 39.6 | 59.9 | 82.0 | 87.0 |
| GCA | 13.7 | 65.3 | 78.7 | 89.7 | 93.1 |
| GCU | — | | | 64.3 | 74.8 |
| $I^{15.1}$ $G^{15.2}$ Catalytic oligomer | | | | | |
| CCC | — | | | 34.33 | 45.38 |
| CCA | 1.1 | 18.8 | 45.5 | 70.8 | 80.63 |
| CCU | 2.0 | | | 28.4 | 36.7 |
| $I^{15.1}$ $A^{15.2}$ Catalytic oligomer | | | | | |
| UCC | 6.8 | | | 57.0 | 64.7 |
| UCA | 1.6 | | | 39.6 | 60.8 |
| UCU | 3.3 | | | 41.1 | 53.1 |
| $A^{15.1}$ $C^{15.2}$ Catalytic oligomer | | | | | |
| GUC | 1.6 | 38.5 | 66.5 | 93.5 | |

The numbers represent the percentage of substrate cleaved at the indicated time point (which were at 0, 10, 30, 60, and 120 minutes after starting the reaction). The results indicate that substrates with a C at position 16.1 are able to be cleaved by catalytic oligomers containing an I at position 15.1. While there are differences between the various substrates at the 120 minute time point, the data show that a substrate with a C at position 16.1 in conjunction with a catalytic oligomer with an I at position 15.1 is able to effectively cleave in all backgrounds, indicating that the substitution of an I at position 15.1 does in fact allow for the cleavage of any appropriate substrate containing a $N^{16.2}C^{16.1}H^{17}$ site.

Initial rates of cleavage of the twelve substrates having $C^{16.1}$, and the control substrate having $U^{16.1}$, by the corresponding catalytic oligomers (all shown in Table 1) were determined using single turnover kinetics. Single turnover kinetics were assessed by mixing 2.5 μl of a 100 μM ribozyme solution, 2.5 μl of a 10 μM solution of 5' fluorescein labeled substrate, and 10 μl of a 100 mM Tris-HCl pH 7.4 solution. The mixture was diluted to a fmal volume of 90 μl, heated to 95° C. for 5 minutes, and cooled to 37° C. The reaction was started by adding 10 μl of a 100 mM $MgCl_2$ solution. The final concentrations of the reaction components were 250 nM substrate, 2.5 μmol ribozyme, and 10 mM $MgCl_2$. Ten microliter samples were removed at various times and mixed with 10 μl of a 100 mM EDTA, bromphenol blue solution to stop the reaction. Cleavage products were separated from unreacted substrate by PAGE and were quantitated on a Molecular Dynamics Fluorescence Imager.

The data, measured in fraction of substrate cleaved versus time, were fitted to the equation:

$$\text{frac}[P] = H_0(1 - e^{-k_2 t})/S_0$$

as described by Jankowsky and Schwenzer, *Nucl. Acids Res.* 24:433 (1996). The calculated values of $k_2$ for the various ribozymes are shown in Table 3.

TABLE 3

| $N^{16.2}N^{16.1}H^{17}$ Triplet | $k_2$ (min$^{-1}$) | Substrate sequence | |
|---|---|---|---|
| | | gcgacccuGAuGaggccgugaggccGaaIuauuc*T | (SEQ ID NO:17) |
| ACC | 0.07 | Fl-GAAUACCGGUCGC*T | (SEQ ID NO:4) |
| ACA | 0.36 | Fl-GAAUACAGGUCGC*T | (SEQ ID NO:5) |
| ACU | 0.026 | Fl-GAAUACUGGUCGC*T | (SEQ ID NO:6) |
| | | gcgacccuGAuGaggccgugaggccGaaIcauuc*T | (SEQ ID NO:18) |
| GCC | 0.12 | Fl-GAAUGCCGGUCGC*T | (SEQ ID NO:7) |
| GCA | 0.48 | Fl-GAAUGCAGGUCGC*T | (SEQ ID NO:8) |
| GCU | 0.05 | Fl-GAAUGCUGGUCGC*T | (SEQ ID NO:9) |
| | | gcgacccuGAuGaggccgugaggccGaaIgauuc*T | (SEQ ID NO:19) |
| CCC | <0.01 | Fl-GAAUCCCGGUCGC*T | (SEQ ID NO:10) |
| CCA | 0.04 | Fl-GAAUCCAGGUCGC*T | (SEQ ID NO:11) |
| CCU | <0.01 | Fl-GAAUCCUGGUCGC*T | (SEQ ID NO:12) |
| | | gcgacccuGAuGaggccgugaggccGaaIaauuc*T | (SEQ ID NO:20) |
| UCC | <0.01 | Fl-GAAUUCCGGUCGC*T | (SEQ ID NO:13) |
| UCA | <0.01 | Fl-GAAUUCAGGUCGC*T | (SEQ ID NO:14) |
| UCU | <0.01 | Fl-GAAUUCUGGUCGC*T | (SEQ ID NO:15) |
| | | gcgacccuGAuGaggccgugaggccGaaAcauuc*T | (SEQ ID NO:21) |
| GUC | 0.13 | Fl-GAAUGUCGGUCGC*T | (SEQ ID NO:16) |

Fl = Fluorescein label
*T = 3'-3' inverted thymidine
A, C, G, I, U = ribonucleotides (I is inosine)
a, c, g, u = 2'-O-allyl-ribonucleotides The results show that substrates with $A^{16.2}C^{16.1}H^{17}$ and $G^{16.2}C^{16.1}H^{17}$ triplets are cleaved at a high rate. Comparison to the control catalytic oligomer having an A at position 15.1 (to cleave a substrate with a $G^{16.2}U^{16.1}C^{17}$ triplet) shows that substrates with $A^{16.2}C^{16.1}A^{17}$ and $G^{16.2}C^{16.1}A^{17}$ triplets (to be cleaved by a catalytic oligomer with an I at position 15.1) have an initial rate of cleavage that is higher than the corresponding control reactions involving reactants with a standard $A^{15.1}$-$U^{16.1}$ base pair.

Publications cited herein and the material for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A composition that induces cleavage of an RNA substrate, the composition comprising:

$5'-Z_1-Z_2-Z_3-3'$ wherein $Z_1$ and $Z_3$ are oligomeric sequences which (1) are comprised of nucleotides, nucleotide analogues, or both, or (2) are oligonucleotide analogues, wherein the oligomeric sequences specifically interact with the RNA substrate by hybridization, wherein $Z_2$ consists of
$5'-X^{12}X^{13}X^{14}X^{15.1}-3'$, or
$5'-X^{\wedge 12}X^{12}X^{13}X^{14}X^{15.1}-3'$, wherein $Z_2$ is comprised of nucleotides, nucleotide analogues, or both, wherein the nucleotides and nucleotide analogues each have the structure

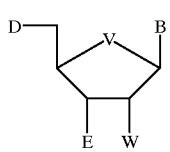

(I)

wherein each B is independently adenin-9-yl, cytosin-1-yl, guanin-9-yl, uracil-1-yl, uracil-5-yl, hypoxanthin-9-yl, thymin-1-yl, 5-methylcytosin-1-yl, 2,6-diaminopurin-9-yl, purin-9-yl, 7-deazaadenin-9-yl, 7-deazaguanin-9-yl, 5-propynylcytosin-1-yl, 5-propynyluracil-1-yl, isoguanin-9-yl, 2-aminopurin-9-yl, 6-methyluracil-1-yl, 4-thiouracil-1-yl, 2-pyrimidone-1-yl, quinazoline-2,4-dione-1-yl, xanthin-9-yl, $N^2$-dimethylguanin-9-yl or a functional equivalent thereof, wherein each V is independently an O, S, NH, or $CH_2$ group, wherein each W is independently selected from the group consisting of —H, —OH, —COOH, —$CONH_2$, —$CONHR^1$, —$CONR^1R^2$, —$NH_2$, —$NHR^1$, —$NR^1R^2$, —$NHCOR^1$, —SH, $SR^1$, —F, —$ONH_2$, —$ONHR^1$, —$ONR^1R^2$, —NHOH, —$NHOR^1$, —$NR^2OH$, —$NR^2OR^1$, substituted or unsubstituted $C_1$–$C_{10}$ straight chain or branched alkyl, substituted or unsubstituted $C_2$–$C_{10}$ straight chain or branched alkenyl, substituted or unsubstituted $C_2$–$C_{10}$ straight chain or branched alkynyl, substituted or unsubstituted $C_1$–$C_{10}$ straight chain or branched alkoxy, substituted or unsubstituted $C_2$–$C_{10}$ straight chain or branched alkenyloxy, and substituted or unsubstituted $C_2$–$C_{10}$ straight chain or branched alkynyloxy, wherein the substituents are independently halogen, cyano, amino, carboxy, ester, ether, carboxamide, hydroxy, or mercapto, wherein $R^1$ and $R^2$ are, independently, substituted or unsubstituted alkyl, alkenyl, or alkynyl groups, where the substituents are independently halogen, cyano, amino, carboxy, ester, ether, carboxamide, hydroxy, or mercapto, wherein D and E are residues which together form a phosphodiester or phosphorothioate diester bond between adjacent nucleosides or nucleoside analogues or together form an analogue of an internucleosidic bond, wherein in $X^{15.1}$, B is hypoxanthin-9-yl, wherein in $X^{12}$, B is independently guanin-9-yl, hypoxanthin-9-yl or 7-deazaguanin-9-yl;

wherein in $X^{13}$ and $X^{14}$, B is independently adenin-9-yl, 2,6-diaminopurin-9-yl, purin-9-yl or 7-deazaadenin-9-yl;

wherein in $X^{\wedge 12}$, B is independently adenin-9-yl, cytosin-1-yl, guanin-9-yl, uracil-1-yl, uracil-5-yl, hypoxanthin-9-yl, thymin-1-yl, 5-methylcytosin-1-yl, 2,6-diaminopurin-9-yl, purin-9-yl, 7-deazaadenin-9-yl, 7-deazaguanin-9-yl, 5-propynylcytosin-1-yl, 5-propynyluracil-1-yl, isoguanin-9-yl, 2-aminopurin-9-yl, 6-methyluracil-1-yl, 4-thiouracil-1-yl, 2-pyrimidone-1-yl, quinazoline-2,4-dione-1-yl, xanthin-9-yl, $N^2$-dimethylguanin-9-yl or a functional equivalent thereof.

2. The composition of claim 1 wherein the RNA substrate comprises $5'-Z_3'-C^{16.1}X^{17}-S-Z_4-Z_1'-3'$, wherein $Z_1'$ and $Z_3'$ interact with $Z_1$ and $Z_3$ by hybridization, wherein $C^{16.1}$ is cytidine, wherein $X^{17}$ is adenosine, guanosine, cytidine, or uridine, wherein S comprises a sequence capable of forming a hairpin structure, wherein cleavage occurs 3' of $X^{17}$, wherein $Z_4$ consists of
$5'-X^3X^4X^5X^6X^7X^8X^9-3'$, or
$5'-X^3X^4X^5X^6X^7X^8X^9X^{9\wedge}-3'$ wherein $X^5$ and $X^8$ are guanosine, wherein $X^6$ and $X^9$ are adenosine, wherein $X^4$ is uridine, wherein $X^3$ is cytidine, and wherein $X^7$ and $X^{9\wedge}$ are independently adenosine, guanosine, cytidine, or uridine.

3. The composition of claim 2 wherein $X^{17}$ is adenosine, cytidine, or uridine.

4. The composition of claim 1, wherein $Z_1$ and $Z_3$ do not contain any pyrimidines that are ribonucleotides.

5. The composition of claim 1, wherein $Z_1$ and $Z_3$ do not contain any ribonucleotides.

6. The composition of claim 1, wherein $Z_1$ and $Z_3$ are comprised of nucleotides, nucleotide analogues, or both, wherein the nucleotides and nucleotide analogues each have the structure

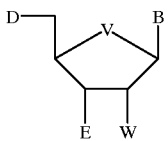

wherein each B is independently adenin-9-yl, cytosin-1-yl, guanin-9-yl, uracil-1-yl, uracil-5-yl, hypoxanthin-9-yl, thymin-1-yl, 5-methylcytosin-1-yl, 2,6-diaminopurin-9-yl, purin-9-yl, 7-deazaadenin-9-yl, 7-deazaguanin-9-yl, 5-propynylcytosin-1-yl, 5-propynyluracil-1-yl, isoguanin-9-yl, 2-aminopurin-9-yl, 6-methyluracil-1-yl, 4-thiouracil-1-yl, 2-pyrimidone-1-yl, quinazoline-2,4-dione-1-yl, xanthin-9-yl, $N^2$-dimethylguanin-9-yl or a functional equivalent thereof, wherein each V is independently an O, S, NH, or $CH_2$ group, wherein each W is independently selected from the group consisting of substituted or unsubstituted $C_1$–$C_{10}$ straight chain or branched alkyl, $C_2$–$C_{10}$ straight chain or branched alkenyl, $C_2$–$C_{10}$ straight chain or branched alkynyl, $C_1$–$C_{10}$ straight chain or branched alkoxy, $C_2$–$C_{10}$ straight chain or branched alkenyloxy, and $C_2$–$C_{10}$ straight chain or branched alkynyloxy, wherein D and E are residues which together form a phosphodiester or phosphorothioate diester bond between adjacent nucleosides or nucleoside analogues or together form an analogue of an internucleosidic bond.

7. The composition of claim 1, wherein $Z_1$ and $Z_3$ each independently contain from 3 to 40 nucleotides, nucleotide analogues, or a combination.

8. The composition of claim 1, wherein $Z_2$ contains one or several nucleotide analogues wherein each W is independently selected from the group consisting of $C_1$–$C_5$ straight chain or branched alkyl, $C_2$–$C_5$ straight chain or branched alkenyl, $C_2$–$C_5$ straight chain or branched alkynyl, $C_1$–$C_5$ straight chain or branched alkoxy, $C_2$–$C_5$ straight chain or branched alkenyloxy, and $C_2$–$C_5$ straight chain or branched $C_2$–$C_5$ alkynyloxy.

9. The composition of claim 1, wherein the free 3' end is protected against exonuclease degradation.

10. The composition of claim 1, wherein in $X^{12}$ W is independently $NH_2$, OH-substituted $C_1$–$C_4$ alkyl, OH-substituted $C_2$–$C_4$ alkenyl, OH-substituted $C_1$–$C_4$ alkoxy or OH-substituted $C_2$–$C_4$ alkenyloxy.

11. The composition of claim 10, wherein in $X^{12}$ W is independently $NH_2$, methoxy, 2-hydroxyethoxy, allyloxy or allyl.

12. The composition of claim 1, wherein $X^{12}$ is a ribonucleotide.

13. The composition of claim 1, wherein $X^{13}$ and $X^{14}$, or a combination is a nucleotide analogue in which each W is independently $C_1$–$C_4$ alkyl, $C_2$–$C_4$ alkenyl, $C_1$–$C_4$ alkoxy, $C_2$–$C_4$ alkenyloxy, OH-substituted $C_1$–$C_4$ alkyl, OH-substituted $C_2$–$C_4$ alkenyl, OH-substituted $C_1$–$C_4$ alkoxy, or OH-substituted $C_2$–$C_4$ alkenyloxy.

14. The composition of claim 13, wherein $X^{13}$ and $X^{14}$, or a combination is a nucleotide analogue in which each W is independently methoxy, 2-hydroxyethoxy or allyloxy.

15. The composition of claim 1, wherein the RNA substrate is selected from the group consisting of human dopamine D2 receptor mRNA, human brain cholecystokinin receptor mRNA, human serotonin 5-HT3 receptor mRNA, human alpha-2-macroglobulin receptor RNA, human tyrosine kinase-type receptor (HER2) mRNA, human interleukin 2 receptor beta chain mRNA, human MAD-3 mRNA, human bcl-1 mRNA, human bcl-2 mRNA, human cyclin F mRNA, human cyclin G1 mRNA, human bleomycin hydrolase mRNA, human acute myeloid leukemia 1 oncogene mRNA, human polycystic kidney disease 1 protein (PKD1) mRNA, transcripts of the bovine viral diarrhea virus, transcripts of the foot and mouth disease virus 3D gene and transcripts of the Epstein-Barr virus.

16. The composition of claim 1, wherein $X^{15.1}$ is a ribonucleotide.

* * * * *